US005637454A

United States Patent [19]
Harley

[11] Patent Number: 5,637,454
[45] Date of Patent: Jun. 10, 1997

[54] ASSAYS AND TREATMENTS OF AUTOIMMUNE DISEASES

[75] Inventor: John B. Harley, Oklahoma City, Okla.

[73] Assignee: Oklahoma Medical Research Foundation, Oklahoma City, Okla.

[21] Appl. No.: 335,198

[22] Filed: Nov. 7, 1994

Related U.S. Application Data

[63] Continuation of Ser. No. 648,205, Jan. 31, 1991, abandoned, which is a continuation-in-part of Ser. No. 472,947, Jan. 31, 1990, abandoned.

[51] Int. Cl.[6] .......................... G01N 33/564; G01N 33/569

[52] U.S. Cl. .............................. 435/5; 435/7.24; 436/506

[58] Field of Search .............................. 435/5, 7.24, 7.31, 435/7.32; 436/506; 530/388.35, 388.4, 388.5, 389.4, 389.5

[56] References Cited

U.S. PATENT DOCUMENTS

| | | | |
|---|---|---|---|
| 4,865,970 | 9/1989 | Brot et al. | 435/7 |
| 5,354,691 | 10/1994 | Van Eden et al. | 436/506 |

FOREIGN PATENT DOCUMENTS

| | | |
|---|---|---|
| 0313156 | 4/1989 | European Pat. Off. . |
| WO 88/09932 | 6/1988 | WIPO . |
| WO 91/11718 | 8/1991 | WIPO . |

OTHER PUBLICATIONS

Ferris and Donaldson, *Veterinary Microbiology* vol. 18 No. 3–4, pp. 243–258 (1988).

Mosier, et al., *Nature* vol. 335, pp. 256–259 (1988).

Tigbe, *Production of Human rheumatoid factors (RF) by SCID mice transplanted with synovial membrane lymphocytes*, presented at the Arthritis Foundation Fellows Conference, Amelia Island, Plantation, Florida, Dec. 8–10, 1989.

Guldner, et al., *The Journal of Immunology*, vol. 141, No. 2, pp. 469–475 (Jul. 15, 1988).

Schaack, pp. 581–588, In *Annals of Internal Medicine* vol. 111, No. 7, pp. 581–591 (Oct. 1, 1989).

Scofield and Harley, *Proceedings of the National Academy of Sciences U.S.A.* vol. 88, pp. 3343–3347 (Apr. 15, 1991).

T. Dyrberg et al, *Current Topics in MicroBiology and Immunology*, vol. 130, 25–37, 1986.

H. M. Geysen et al, *Jour. Immunol. Meth.*, 102, 259–274, 1987.

Ben–Chetrit E., Et al., "Isolation and Characterization of a cDNA Clone Encoding the 60–kD Component of the Human SS–A/Ro Ribonucleoprotein Autoantigen", *J. Clin. Invest.*, 83(4):128401292 (1989).

Chambers, J.C., et al., "Isolation and Analysis of cDNA Clones Expressing Human Lupus La Antigen", *Proceed. Nat. Acad. Sci.*, 82(7):2115–2119 (1985).

Chambers, J.C., et al., "Genomic Structure and Amino Acid Sequence Domains of the Human La Autoantigen", *Journal of Biological Chemistry*, 263(34):18043–18051 (1988).

Chan, E.K.L., et al., "Ribonucleoprotein SS–B/La Belongs to a Protein Family with Consensus Sequence for RNA Binding", *Nucleic Acids Research*, 17(6):2233–2244 (1989).

Crone, et al., "Viral Transcription is Necessary and Sufficient for Vesicular Stomatis Virus to Inhibit Maturation of Small Nuclear Ribonucleoproteins", *Journal of Virology*, 63(10):4172–4180 (1989).

Cunningham, et al., "Human Monoclonal Antibodies Reactive with Antigens of the Group A Streptococcus and Human Heart", *Journal of Immunology*, 141(8):2760–2766, (1988).

Deutscher, S.L., et al., "Molecular Analysis of the 60–kDa Human Ro Ribonucleoprotein", *Proceed. Nat. Acad. Sci.*, 85(24):9479–9483 (1988).

Elkon, K.B., et al., "Epitope Mapping of Recombinant HeLa SmB and B' Peptides Obtained by the Polymerase Chain Reaction", *Journal of Immunology*, 145(2):636–643 (1990).

Harley, et al., "Gene Interaction at HLA–DO Enhances Autoantibody Production in Primary Siorgren's Syndrome", *Science*, 232:1145–1147 (1986).

Kurilla, et al., "The Leader RNA of Vesicular Stomatis Virus is Bound by a Cellular Protein Reactive with Anti–La Lupus Antibodies", *Cell*, 34:837–845 (1983).

McAllister, G., et al., "cDNA Sequence for the Rat U snRNP–Associated Protein N:Description of a Potential Sm Epitope", *EMBO Journal*, 8(4):1177–1181 (1989).

Renz, M., et al., "Expression of the Major Human Ribonucleoprotein (RNP) Autoantigens of *Escherichia coli* and Their Use in an EIA for Screening Sera from Patients with Autoimmune Diseases", *Clinical Chemistry*, 35(9):1861–1863 (1989).

Rokeach, L.A., et al., "Primary Structure of a Human Small Nuclear Ribonucleoprotein Polypeptide as Deduced by cDNA Analysis", *Journal of Biological Chemistry*, 264(9):5024–5030 (1989).

(List continued on next page.)

*Primary Examiner*—David Saunders
*Attorney, Agent, or Firm*—Arnall Golden & Gregory

[57] ABSTRACT

A specific method has been developed to identify the etiologic or immunogenic agent responsible for the production of autoantibodies characteristic of a particular disorder or immune response. The antigen is first isolated, then divided into overlapping short amino acid sequences. The sequences having the greatest reactivity with the autoantibodies are identified and compared with all known amino acids sequences using the available computer data bases. The protein having the maximum number of sequences homologous to the sequences of greatest reactivity with the autoantibodies is the likeliest candidate for the etiological agent. Applying this method, it has been determined that the etiological agent for the production of anti-Ro/SSA autoantibodies characteristic of numerous autoimmune diseases such as SLE appears to be a virus highly homologous to the Indiana strain of the vesicular stomatitis virus. Once the etiologic agent and antigenic sequences are known, it is possible to design assays and reagents for the diagnosis and treatment of patients having either the etiological agent and/or autoantibodies. An animal model has been developed for studying the mechanisms of, and screening compounds for the treatment or prevention of, the expression of these autoantibodies.

11 Claims, 6 Drawing Sheets

OTHER PUBLICATIONS

Scofield, et al., "60 kD Ro/SSA Autoepitopes are Found in Regions of Homology Between Ro/SSA and the Nucleoapsid Protein of Vesicular Stomatis Virus", *Arthritis and Rheumatism*, 33(9):S101, (1990).

Scofield, et al., "The Autoantigenicity of Human 60kD Ro/SSA is related to Homologies Between ro/SSA and the Nucleocapsid Protein of Vesicular Stomatis Virus", *Clinical Research*, 38(2):316A, (1990).

Sharpe, N.G., et al., "Isolation of cDNA Clones Encoding the Human Sm B/B' Autoimmune Antigen and Specifically Reacting with Human Anti-Sm Autoimmune Sear", *FEBS Letters*, 250(2):585–590 (1989).

Sillekens, P.T.G., et al., "cDNA Cloning of the Human U1 snRNA-Associated A Protein: Extensive Homology Between U1 and U2 snRNP-Specific Proteins", *EMBO Journal*, 6(12):3841–3848 (1987).

Sturgess, A.D., et al., "Characteristics and Epitope Mapping of a Cloned Human Autoantigen La", *Journal of Immunology*, 140(9):3212–3218 (1988).

Yamamoto, K., et al., "Isolation and Characterization of a Complementary DNA Expressing Human U1 Small Nuclear Ribonucleoprotein C Polypeptide", *Journal of Immunology*, 140(1):311–317 (1988).

A. K. Banerjee et al, *Virlogy*, 137, 432–438 (1984).

I. R. Cohen, *Scientific American*, 258, 52–60, 1988.

N. J. Depolo et al, *J. Virology*, 61, 454–464, 1987.

C. J. Gallione et al, *J. Virology*, 39, 529–535, 1981.

W. J. Herbert et al, *Dictionary of Immunology*, 3rd ED., Blackwell Scientific Publications, Oxford, UK, 1985, p. 14.

FIGURE 5

| | | | | | | | | | | |
|---|---|---|---|---|---|---|---|---|---|---|
| Ro/SSA | 52 57<br>K*L*GLEN | 133 136<br>KDLK | 185 189<br>LSHL*K | 237 241<br>RTKD*E | 264 267<br>KSKE | 278 283<br>LTALL*R | 337 342<br>RGKL*K*W | 350 354<br>LKALD | 406 410<br>TEKD*S | 485 491<br>EYRKK*MD |
| VSV-IND#1 | | | | | KSKE<br>34 37 | LTALLtR<br>303 309 | RGKLdKdW<br>81 88 | LKALD<br>110 114 | | EYRKKtMD<br>151 158 |
| VSV-IND#2 | | | | | KSKE<br>34 37 | LTALLtR<br>303 309 | RGKLdKdW<br>81 88 | | | EYRKKtMD<br>151 158 |
| VSV-NJ | KtLdGLEN<br>155 162 | | | | | | | | TEKDdS<br>357 362 | YRKK<br>152 155 |
| VSV-Chand. | | | LSHLqK<br>232 237 | RTKDaE<br>168 173 | | | | | EKD*S<br>359 362 | |
| Rabies | | KDLK<br>34 37 | | | | | | | | |

60S 250 255 76 79
ALSVETEKLL
ALSVETEKLL
Ro 217 226
311 314

FIGURE 6a 69 77
B27 AKAQTDRED
KLEB AKAQTDRED
188 193
51 54

FIGURE 6b

ASSAYS AND TREATMENTS OF AUTOIMMUNE DISEASES

This is a continuation of U.S. Ser. No. 07/648,205 filed on Jan. 31, 1991, now abandoned, which is a continuation in part of U.S. Ser. No. 07/472,947 entitled "Assays and Treatments for Autoimmune Disease" filed Jan. 31, 1990 by John B. Harley, now abandoned.

BACKGROUND OF THE INVENTION

This invention is in the area of the prevention, diagnosis and treatment of autoimmune diseases, especially systemic lupus erythematosus.

The United States government has rights in this invention by virtue of grants from the National Institutes of Health and the Veteran's Administration.

Systemic lupus erythematosus (SLE) is similar to many other disorders in which autoantibodies are found and thought to be important in etiology and pathogenesis. SLE can be grouped with those diseases that commonly have autoantibodies present but for whom a central role of autoantibody in pathogenesis leading to clinical expression has yet to be fully established or accepted. Other such diseases include Sjogren's syndrome, rheumatoid arthritis, juvenile onset diabetes mellitus, primary biliary cirrhosis, Wegener's granulomatosis, inflammatory bowel disease, and many others.

Typically, autoimmune diseases present with a wide array of symptoms and clinical signs. The production of circulating autoantibodies to ribonucleoprotein complexes (RNPs) is a unifying characteristic of some of the rheumatic autoimmune diseases. The most common antigens in SLE and closely related disorders include: Ro/SSA, La/SSB, nRNP and Sin. Initially, these antibodies were found using double immunodiffusion, but more recently sensitive solid phase assays have been developed to quantitate the autoantibodies. The Ro/SSA RNA-protein particle has been found to be a constituent of all human cells evaluated to date. Approximately half of Sjogren's syndrome and systemic lupus erythematosus (SLE) patients have anti-Ro/SSA precipitins. Approximately 75% of patients with subacute cutaneous lupus erythematosus or complement component C2 deficiency with SLE have anti-Ro/SSA precipitins. Over 80% of mothers of newborns with neonatal lupus dermatitis or complete congenital heart block have this autoantibody. As many as 5% of patients with rheumatoid arthritis, polymyositis, and progressive systemic sclerosis have anti-Ro/SSA, as reported by R. M. Bernstein, et al., *Mol, Biol. Med.* 2:105–120 (1984); and J. B. Harley and K. K. Gaither, *Autoantibodies*. In Rheumatic Disease Clinics of North American: Systemic Lupus Erythematosus 14:1, 43–56 (1988).

It has been an issue of intensive debate as to whether the many autoantibodies found in systemic lupus erythematosis and related diseases represent an antigen specific or a polyclonal, antigen non-specific response. Evidence that autoantibodies are important in the expression of SLE and related syndromes is convincing. Specific depletion in a heart block neonate (Harley, J. B., et al., *Arthritis Rheum.*28:1321–1325 (1985)) and specific anti-Ro/SSA immunoglobin deposition in human skin (Lee, L. A., et al., *J. Clin. Invest.* 83:1556–1562 (1989)) have been demonstrated. Specific concentration of anti-Ro/SSA has been shown in the immunoglobulin of renal eluates from kidneys affected by lupus nephritis (Maddison, P. J. and Reichlin, M. *Arthritis Rheum.* 22:858–863 (1979)). Anti-Ro/SSA has been found to be specifically concentrated in a parotid gland of a patient with Sjogren's syndrome and primary biliary cirrhosis (Penner, E. and Reichlin, M. *Arthritis Rheum.* 25:1250–1253 (1982)). Observations that infants with transplacentally acquired maternal IgG develop neonatal lupus dermatitis and/or complete congenital heart block (Harley, J. B. and Gaither, K. K.: *Autoantibodies*. In Rheumatic Disease Clinics of North America: Systemic Lupus Erythematosus 14:1,43–56 (1988)) strongly suggests that maternal autoantibody (anti-Ro/SSA or anti-La/SSB) transported across the placenta is a critical component required, but not sufficient, for these clinical problems.

It has also been shown that some normal individuals have low levels of anti-Ro/SSA, that some normal family members of SLE patients have anti-Ro/SSA, and that 1% of normal pregnant women, and 0.1% of a cohort of hospitalized patients have precipitating levels of this autoantibody K. K. Gaither, et al., *J. Clin. Invest.* 79:841–846 (1987); T. J. A. Lehman, et al., *J. Rheumatol.* 11:644–647 (1987); M. Calmes and B. A. Bartholomew, *J. Clin. Pathol.* 38:73–75 (1985); P. J. Maddison, et al., *J. Rheumatol.* 5:407–411 (1978)). Even if the anti-Ro/SSA autoantibody is not pathogenic, the concentrations of anti-Ro/SSA autoantibody achieved by patients can be extraordinary, and is commonly higher than 1 mg/ml of specific anti-Ro/SSA immunoglobulin (K. K. Gaither and J. B. Harley, *Prot. Biol. Fluids Proc. Colloq.* 33:413–416 (1985); J. B. Harley, et al., *Arthritis Rhuem.* 29:196–206 (1986)). The immune system derangement leading to this specific overproduction of anti-Ro/SSA is not apparent but is likely to reflect a fundamental mechanism related to the immunopathogenesis of the related diseases.

The Ro/SSA family of proteins has now been shown to have several molecular forms which are operationally defined by the molecular weight of the antigen identified. A major form has an apparent molecular weight of 60 kiloDaltons (kD). This protein is associated with one of four hY RNAs. Recently, two additional proteins bound by anti-Ro/SSA sera have been identified by M. D. Rader, et al., *J. Clin. Invest.* 83:1556–1562 (1989), with molecular weights of 52 kD and 54 kD. A 48 kD protein, calmodulin, has been identified as being bound by anti-Ro/SSA sera (McCauliffe, et al., *J. Clin. Invest.* 85:1379–1391 (1990)). The La/SSB protein, a 48 kD peptide, as described by J. C. Chambers and J. D. Keene, *Proc. Natl. Acad. Sci. USA* 82:2115–2119 (1985), is also a member of this group of autoantibodies, and binds small RNAs with a polyuridine terminus, as reported by J. E. Stephano, *Cell* 36:145–154 (1984). La/SSB is bound by a third of the anti-Ro/SSA precipitin positive sera. Anti-Ro/SSA autoimmune sera and heteroimmune rabbit sera have been used to demonstrate different specificities for lymphocyte Ro/SSA and red blood cell Ro/SSA. While several specificities have been noted for the Ro/SSA RNP, very little information exists defining the specific epitopes involved in the autoimmune response.

It is therefore an object of the present invention to provide methods for identifying immunogens, and the specific epitopes and sequences encoding the epitopes, which elicit the production of an autoimmune response involving antigens or autoantigens that are bound by immunoglobulin, antigen-specific B cell surface receptor molecules, or the antigen-specific T cell receptor.

It is a further object of the present invention to provide assays and diagnostic reagents for identifying individuals previously exposed to a particular immunogen or expressing these autoantibodies, or the epitopes (or their immune equivalent) eliciting production of the autoantibodies.

It is a still further object of the present invention to provide methods and compositions for identifying and treating autoimmune disorders, including such diverse diseases as Sjogren's syndrome, rheumatoid arthritis, juvenile onset diabetes mellitus, primary biliary cirrhosis, Wegener's granulomatosis, inflammatory bowel disease, potentially autoimmune disorders, or any other disease having immune manifestations.

It is a still further object of the present invention to provide a procedure to determine the immunologic origin of autoimmune manifestations of diseases.

It is another object of the present invention to provide an animal model expressing human autoantibodies for screening therapeutics.

It is yet another object of the present invention to provide a procedure to determine the origin of selected manifestations of diseases of known etiology.

SUMMARY OF THE INVENTION

A specific method has been developed to identify the etiologic or antigenic agent responsible for the production of autoantibodies characteristic of a particular disorder. The antigen is first isolated, using, for example, autoantibodies isolated from one or more patients. The antigen is then divided into overlapping short amino acid sequences, preferably twenty amino acids or less, octapeptides in the example described below for Ro/SSA and La/SSB. The sequences having the greatest reactivity with the autoantibodies are identified. These sequences are then compared with all known amino acids sequences using the available computer data bases. The protein having the maximum number or proportion of sequences homologous to the sequences of greatest reactivity with the autoantibodies is among the likeliest candidate of the known sequenced proteins for the etiological agent or immunogen.

Applying this method, it has been determined that the etiological agent for the production of several autoantibodies, including the Ro/SSA antigen, characteristic of numerous autoimmune diseases such as SLE, appears to be a virus homologous to the Indiana strain of the vesicular stomatitis virus. The nucleocapsid protein of this virus (N) contains at least six areas identically homologous to the 60 kD Ro/SSA sequence (three pentapeptides, and three quadrapeptides). (There are 23 areas of at least tripeptide homology, based upon identically homologous tripeptides.) While several other protein sequences are known which demonstrate more homology with the 60 kD Ro/SSA than does the N protein, only for these regions of N and Ro/SSA does the antigenicity and homology closely coincide ($p<0.00017$).

Once the etiological agent and antigenic sequences are known, it is possible to design assays and reagents for the diagnosis and treatment of patients having either the etiological agent and/or autoantibodies. An animal model developed by transferring human autoantibody producing cells to mice with severe combined immunodeficiency should be particularly useful in screening compounds for the treatment or prevention of the expression of these and other autoantibodies.

BRIEF DESCRIPTION OF THE DRAWINGS

FIG. 5 shows the areas of homology of at least four sequential amino acids between 60 kD Ro/SSA and rhabdoviral N proteins. Shared small peptides between Ro/SSA and N proteins which overlap central antigenic peptides of Ro/SSA or which may be extended by single amino acid gaps (*) in the Ro/SSA sequence. Vesicular stomatitis virus Indiana serotype (VSV-IND#1) (Gallione, et al., *J. Virol.* 39:529–535 (1981)), VSV-Indiana strain 2 (VSV-IND#2) (DePolo, et al., *J. Virol.* 61:454–464 (1987)) and New Jersey strain (VSV-NJ) (Banerjee, et al., *Virology* 137:432–438 (1984)), Chandipura strain (VSV-Chand)(Masters, et al., *Virology* 157:298–306 (1987)) and rabies virus Tordo, et al., *Nuc. Acid Res.* 14(6):2671–2683 (1986)) are presented. Amino acid residues are presented in the single-letter code and in their order on the 60-kDa Ro/SSA sequence; lower case letters are used where gaps have been introduced in Ro/SSA. Amino acid residues in the Ro/SSA sequence which are part of a central antigenic octapeptide of the reference anti-Ro/SSA serum are indicated by dotted underlines. Shared sequences with no overlap with the central antigenic octapeptides or sequence extension by single amino acid gaps in Ro/SSA are not presented. DEMV is found at residues 417–420 in Ro/SSA and 256–259 in VSV-Ind. DLLR is at 181–184 of Ro/SSA and 258–261 of VSV-Chand. The EVCR peptide from 117–120 of Ro/SSA is the only peptide shared with the Pity strain sequence at 258–261 (Crysler, et al., *J. Gen. Virol.* 71:2191–2194 (1990)). AAAM and DPDD are respectively found at 369–399 and 510–513 in Ro/SSA while at 75–78 and 66–69 in rabies.

FIG. 6 shows two examples of juxtaposition of sequence from different proteins which may have immune and autoimmune regulatory consequences. FIG. 6A shows that the 60 kD Ro/SSA sequence (Ro) between amino acid residues 217 and 226 exactly matches the combined portions of the sequences of the 60S PO protein (PO) between its amino acid sequence residues 250 and 255 followed by residues 76 through 79. A second E K L L sequence is found in Ro/SSA between residues 311 and 314. FIG. 6B shows HLA-B27 amino acid sequence between residues 69 and 77 is exactly matched by the combined regions between residues 51 and 54 in addition to 188 and 193 of the Klebsiella neuramidase protein (KLEB).

DETAILED DESCRIPTION OF THE INVENTION

Figure 1C:
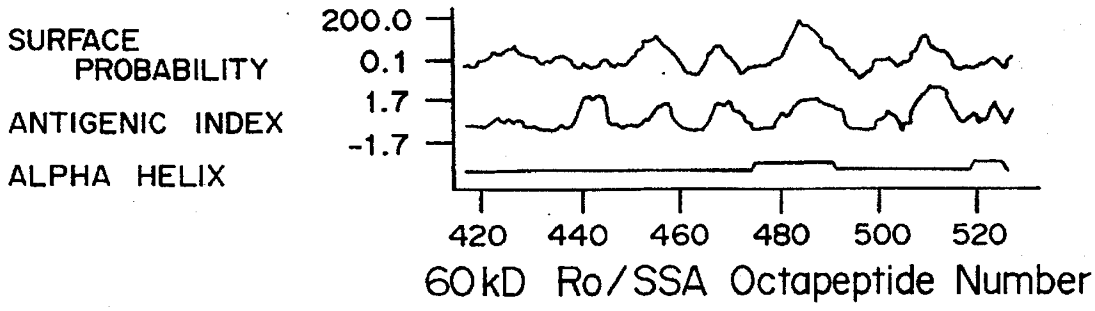
FIG. 1 is a schematic of the properties of the 119 amino acid sequence at the carboxyl terminus of the human 60 kD Ro/SSA protein. Panel A. Predictions of physical characteristics based upon the amino acid sequence from the Wisconsin Genetics Systems software (Devereaux, et al., Sequence analysis software of the genetics computer group. pp. 233–239, University of Wisconsin, Madison, Wis. (1987); Jameson and Wolff *CABIOS* 4:181–187 (1988)). Panel B. Solid phase immunoassay of 119 overlapping octamers at each position of the sequence. Bars represent activity in a solid phase ELISA of an anti-Ro/SSA reference serum that also binds the carboxyl terminal 13 kD peptide of V8 protease digested bovine Ro/SSA Panel C. The background activity in this assay is from a normal control serum. The mean values from two experiments are presented. The octapeptide number is the sequence position of the amino terminal amino acid of the octapeptide.

The present invention is the discovery of a method for identifying an etiologic or antigenic agent for an autoimmune disorder such as SLE, non-self nucleic or amino acid sequences eliciting an immune type response, diagnostics and therapeutics for the prevention and treatment of these disorders. The method is specifically applied to determine the etiologic and/or antigenic and/or immunogenic agent eliciting an autoimmune response in SLE patients. The agent, a virus homologous to vesicular stomatitis virus-Indiana strain (VSV-Ind), was characterized by identity of sequence at areas of antigenicity in the major antigens for autoantibodies characteristic of SLE.

As used herein, autoimmune diseases are diseases that are primarily autoimmune, as well as diseases which do not appear to be primarily autoimmune but have immune manifestations involving immunoglobulins, antigen specific B cell surface receptors, or antigen-specific T cell receptors. Examples of diseases which fall into these categories are SLE, Sjogren's syndrome, rheumatoid arthritis, juvenile onset diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (Type II diabetes), male and female autoimmune infertility, ankylosing spondolytis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, mumps, Evan's syndrome, and autoimmune gonadal failure. Immunization is any procedure occurring leading to a humoral or cellular immune response to a specific substance. An autoantigen is any protein, or portion of a protein specifically recognized by and bound to an autoantibody. An etiologic or antigenic agent is any agent eliciting production of autoantibodies, including infectious agents such as bacteria, viruses, viroids, Rickettsia, and fungi, or environmental agents, including foods or chemicals. An autoantibody is any immunoglobulin, antigen specific B cell surface receptor (surface immunoglobulin), or antigen specific T cell receptor directed against a self-antigen, such as a protein or a nucleic acid. An antibody is any immunoglobulin, antigen specific B cell surface receptor (surface immunoglobulin), or antigen specific T cell receptor directed against a antigen.

The methodology, which can be applied to determine the antigenic or etiologic agent for any autoimmune disorder, potentially autoimmune disease, or disease having immune manifestations, was specifically applied to the determination of an etiologic and/or antigenic agent eliciting autoantibodies such as Ro/SSA in patients having systemic lupus erythematosus (SLE).

The single amino acid code is used in the figures and following examples, as follows:

| | | |
|---|---|---|
| A - alanine | I - isoleucine | R - arginine |
| C - cysteine | K - lysine | S - serine |
| D - aspartic acid | L - leucine | T - threonine |
| E - glutamic acid | M - methionine | V - valine |
| F - phenylalanine | N - asparagine | W - tryptophan |
| G - glycine | P - proline | Y - tyrosine |
| H - histidine | Q - glutamine | |

As used herein, homology between two peptide sequences is defined as having at least three identical or structurally similar contiguous amino acids in common between the two peptides. Contiguous means covalently bound amino acids or amino acids presenting a contiguous sequence to an antibody (i.e., This would also include structures such as the beta pleated sheet where every other amino acid may bind and, hence, every other amino acid of a structure would be identical or structurally similar). Proteins defined as having regions of homology and antigenicity are proteins having at least two contiguous sequences of three or more amino acids in common, based on identity or structural similarity, which react with the same source of antibody.

EXAMPLE 1

Figure 1B:
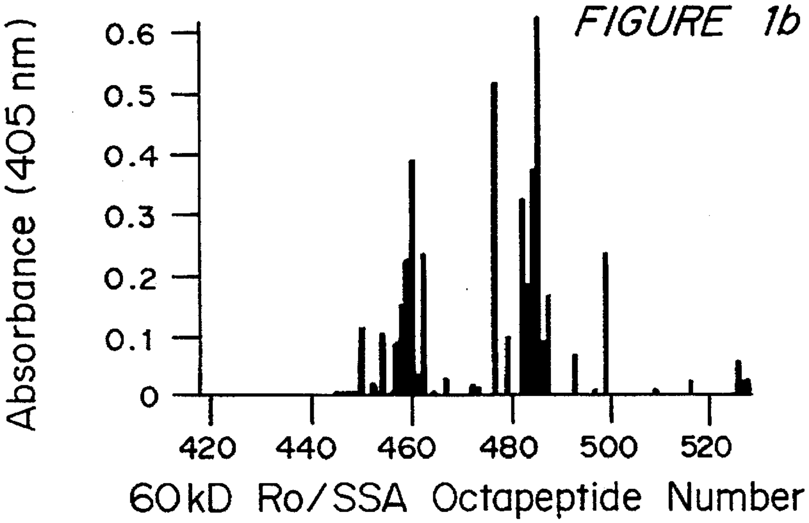
Figure 1A:
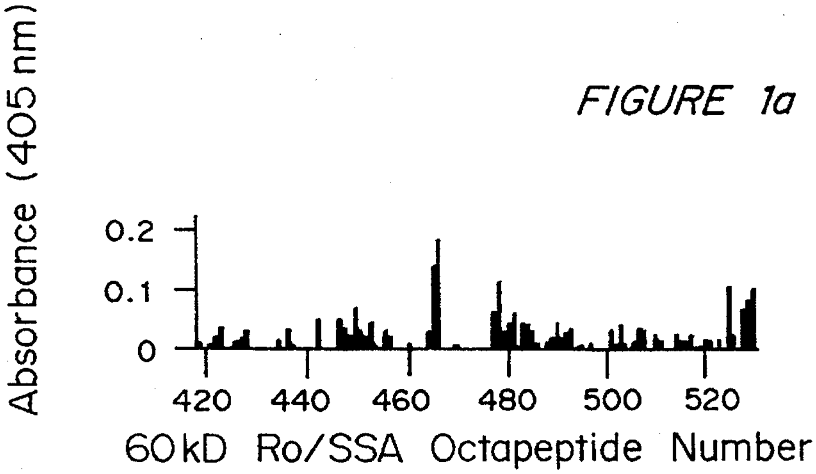

Preparation of Ro/SSA fragments and identification of Peptides reacting with anti-Ro/SSA antibodies Isolation of a major immunoreactive fragment of an autoantigen Highly purified bovine Ro/SSA and selective limited proteolysis with Staphylococcal V-8 protease was used to identify a major immunoreactive fragment with an apparent molecular weight of 13 kD on Western blots with polyclonal rabbit anti-Ro/SSA serum and a reference anti-Ro/SSA patient serum. After electroblotting onto polyvinylidene difiuoride (PVDF) membranes, the 13 kD peptide was partially sequenced. The sequence showed a dose homology to the predicted amino acid sequence from the cloned human cDNA for the Ro/SSA ribonucleoprotein beginning at amino acid residue 419 and continuing through 540. Overlapping octapeptides of the carboxyl terminal portion of Ro/SSA were synthesized which included the 13 kD peptide. An octapeptide with the sequence, E Y R K K M D I (SEQ ID No. 1), demonstrated maximal antigenicity with the reference anti-Ro/SSA serum (FIG. 1 and FIG. 5). The surrounding overlapping peptides were also antigenic but less reactive in ELISA. Two separate antigenic octapeptides with less reactivity and with no overlapping antigenic peptides were also identified.

Specific references for procedures used herein are hereby incorporated by reference.

Antisera to bovine Ro/SSA has been prepared as described by Mamula, et at., *J. Exp. Med.* 86:1889–1901 (1986). New Zealand White rabbits are immunized with 200 mg purified Ro/SSA in complete Freund's adjuvant both intramuscularly and subcutaneously. They have been boosted at 2 weeks and 4 weeks with intravenous injections and bled 10 days later. All human sera used have been obtained from rheumatic disease patients or normal laboratory personnel.

For Staphylococcal V-8 protease digestion of Ro/SSA, purified bovine Ro/SSA was concentrated in 0.1 M ammonium bicarbonate buffer at pH 7.9. Samples were evaporated to dryness and aliquots of *Staphylococcus aureus* protease (Type XVII-S Sigma Chemical, St. Louis, Mo.) were added at an enzyme to Ro/SSA protein ratio of 1:15 (w:w) in the presence of 0.1% sodium dodecyl sulfate, and 50 μg/ml RNAase (Sigma Chemical Co., St. Louis, Mo.). Digests were carded out in a shaking water bath at 37° C for 2 hrs after which they were desiccated under vacuum and stored at −20° C.

A number of proteolytic enzymes were used to fragment the Ro/SSA molecule which yielded different numbers and sizes of immunoreactive peptide fragments. The enzyme which gave the greatest number of immunoreactive peptides in Western blots was Staphylococcal V-8 protease. Under the appropriate pH conditions (at pH 7.8), this enzyme has been shown by Houmard and Drapeau, *Proc. Natl. Acad. Sci. USA* 69:3506–3509 (1972), to cleave rather selectively on the carboxyl side of glutamic acid. A number of different conditions were tested to determine the optimal parameters for digestion of Ro/SSA. Optimal conditions utilized a 1:15 enzyme (V-8 protease) to protein (Ro/SSA) ratio, with 0.1% sodium dodecyl sulfate and RNAase at 50 μg/ml, and digestion at 37° C. for 4 hrs in a gyratory water bath.

Twelve and one-half percent (12.5%) polyacrylamide gels with a 4.5% polyacrylamide stacking gel with 0.2% sodium dodecyl sulfate were employed utilizing discontinuous buffer conditions for analysis of peptides by Western immunoblotting. All samples were boiled in the presence of 4% sodium dodecyl sulfate and 10% 2-mercaptoethanol for 5 min prior to electrophoresis. Digests of purified bovine Ro/SSA were analyzed by 12.5% polyacrylamide gel electrophoresis using the method of Mamula, et al., *J. Exp. Med.* 86:1889–1901 (1986). Protein samples were then electroblotted onto nitrocellulose or polyvinyladine difluride (PVDF) membranes using the procedure of P. Matsudaira, *J. Biol. Chem.* 262:10035–10038 (1987) in a TransBlot apparatus (BioRad Labs, Richmond, Calif.). Transfers were done overnight at 200 mAmps in 0.025M Tris, 0.192M glycine, and 20% methanol, pH 8.3. Nitrocellulose blots were then stained with Fastgreen (0.1%) to validate molecular weight by simultaneously processed standards. After blocking, serum samples containing autoantibodies were diluted and allowed to incubate with gentle agitation for 4 hrs. After washing, specific anti-human or anti-rabbit IgG gamma chain specific (Sigma Chemical Co., St. Louis, Mo.) conjugated to alkaline phosphatase was added (at 1:7500 dilution) in 0.1M Tris, 0.1M NaCl, 0.005M $MgCl_3$ at pH 9.5. Gels were then exposed to substrate, 5-bromo-4-chloro-3-indolyl phosphate and nitroblue tetrazolium (Promega Corporation, Madison, Wis.), for 2–10 minutes, allowing development of bands.

Staphylococcal V-8 protease digests of Ro/SSA (20 μg) were electrophoresed, electroblotted and probed with heteroimmune rabbit sera raised against purified 60 kD Ro/SSA at dilutions of 1:1000. A number of immunoreactive peptides were generated. Strongly immunoreactive peptides were found with molecular weights of 51 kD, 40 kD, 35 kD, 28 Kd and 13 kD, with minor bands at 56 kD, 45 kD, and 22 kD.

Similarly, digests were electrophoresed, electroblotted and probed with human serum (at a 1:100 dilution) from a patient with systemic lupus erythematosus (reference serum). This patient had precipitating antibodies to bovine and human Ro/SSA by double immunodiffusion. Anti-Ro/SSA ELISA revealed a Ro/SSA titer of $4.44\times10^6$ units which is approximately equivalent to 8 or 9 mg of specific anti-Ro/SSA autoantibody per ml of serum, as reported by Gaither and Harley, *Protides Biol. Fluids Proc. Colloq.* 33:413–416 (1985). Major immunoreactive peptides were noted with molecular weights corresponding to 51 kD, 30 kD, 28 kD, and 13 kD. Both the heteroimmune rabbit sera and SLE patient sera defined a major reactive band at 13 kD, which was selected for amino acid sequence analysis. To sequence peptides the band of interest was cut from the polyvanilidine difluride membrane and sequenced directly as described by Matsudaira, *J. Biol. Chem.* 262:10035–10038 (1987).

For sequence analysis, Staphylococcal V-8 protease digests (100 μg/lane) were electrophoresed on 12.5% gels and electroblotted onto polyvinylidene difluoride membranes, which have been shown to provide excellent solid phase support for sequencing in automated gas phase sequenators. The band corresponding to 13 kD was carefully cut from the membrane and sequenced on an automated sequenator, as described by Matsudaira, *J. Biol. Chem.* 262:10035–10038 (1987). The amino acid sequence demonstrates close homology to cloned human Ro/SSA, being identical at 19 of 20 amino acids where sequence data was available, beginning 119 amino acids from the carboxyl terminus of the 60 kD Ro/SSA protein.

Synthesis of short, overlapping octapeptides based on the sequence of the major immunoreactive autoantigen peptide.

Overlapping octamers differing by one sequential amino acid were assembled for the 119 amino acids of the carboxy terminal peptide. The predicted amino acid sequence for the human 60 kD Ro/SSA gene product, reported by Deutscher, et al., *Proc. Natl. Acad. Sci,* 85:9479–9483 (1988), was used as the template to determine the appropriate amino acid sequence. The differences between this sequence and the predicted amino acid sequence from the clone obtained by Ben-Chetrit, et al., *J. Clin. Invest.* 83:1284–1292 (1989), were also included but are not shown in the FIGS. 1, 2 and 3.

The 20 naturally occurring amino acids, all with Fmoc protected primary amino groups and with t-butyl protected side chain groups were used in the synthesis. Octapeptides were synthesized at the tips of radiation derivatized polyethylene rods which were arranged in the format of a 96 well microliter plate (Cambridge Research Biochemicals, Cambridge, UK) as described by Geyson, *Proc. Natl. Acad. Sci. USA* 81:3998–4002 (1984). F-moc, t-butyl amino acid solutions (30 mM) were prepared in N,N-dimethylformamide (DMF) which had 1-hydroxybenzotriazole added to final concentration of 30 mM and dispensed into the wells of a microliter plate as dictated by the known sequence of the human Ro/SSA cDNA. After 18 hrs the pins were then bathed sequentially, once in N,N-dimethylformamide for 5 rain, four times in methanol for 2 rain each, and once in final N,N-dimethylformamide for 5 min. The Fmoc protecting group was then removed from the amino acid added last by a 20% piperidine/DMF bath for 30 minutes. This procedure was repeated until the desired peptides were assembled. Once the desired length was reached, the amino terminal group of each peptide was acetylated by placing the pins in a 5:2:1 (v/v/v) mixture of N,N dimethylformamide:acetic anhydride:triethylamine for 90 min at room temperature. Subsequently, the pins were bathed in N,N-dimethylformamide for 2 rain, four times in methanol for 2 min and then air-dried for 10 min. Finally, side chain amino protecting groups were removed by a 95:2.5:2.5 (v/w/v) of trifluoroacetic acid:phenol:ethanedithiol. Pins were then washed with methylene chloride for 2 min, two times in 5% diisopropylethylene in methylene chloride for 5 min, and repeated methylene chloride for 5 min. After drying for 10 min, pins were placed in distilled $H_2O$ for 2 min, transferred to a methanol bath for 18 hrs and dried under vacuum for 18 hrs.

Solid phase anti-peptide assays were conducted carrying out all steps by lowering the pin blocks into microliter plate wells. First, the pins were blocked with 1% bovine serum albumin (BSA) in PBS with 0.05% Tween (PBS/Tween) and then incubated with sera at 1:100 dilution in 1% BSA in PBS overnight at 4° C. in a humidified closed container. The pin blocks were then washed four times with PBS/Tween for 10 min with vigorous agitation. Then, each pin was incubated with a Staphylococcal protein A-alkaline phosphatase conjugate or an anti-human gamma chain specific IgG from goat also conjugated to alkaline phosphatase (Sigma Chemical Co., St. Louis, Mo.) diluted 1:300 at 4° C. for 18 hrs. Washing was repeated as above prior to incubation of the pins in para-nitrophenyl phosphate disodium. Plates were read at 405 nm with a MicroELISA Reader (Dynatech, Alexandria, Va.).

Classification of octapeptides into groups based on immunoreactivity with anti-autoantigen sera The solid phase assay with the octapeptides covalently bound to the solid phase was used to screen for immunoreactivity against normal human sera, against anti-Ro/SSA serum identifying the 13 kD peptide and against anti-Ro/SSA serum not identifying the 13 kD peptide.

Figure 2C:
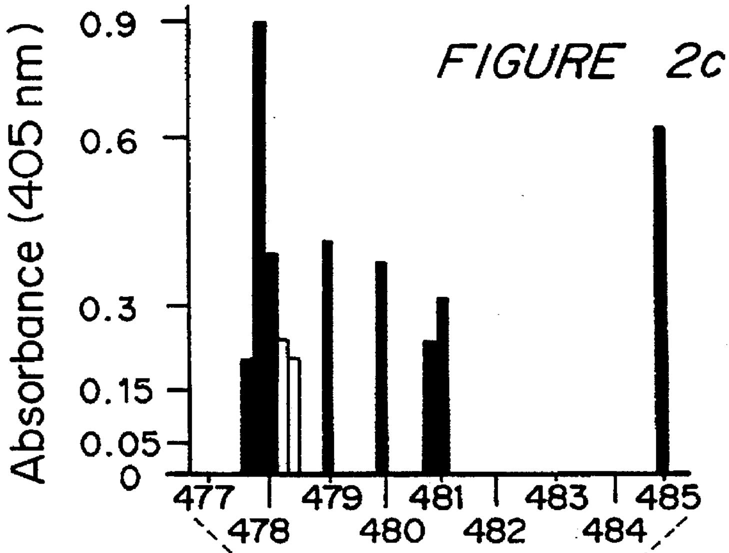
FIG. 2 Panel A presents the log average with respect to binding carboxyl terminal 112 overlapping octapeptides of eight anti-Ro/SSA patients who are positive in Western blot for binding to the 13 kDd peptide of Ro/SSA. Panel B presents patients who are negative for binding the 13 kD peptide. Panel C shows the maximum reactivity of the eight sera which bound the 13 kD peptide (shaded bars) and the two sera which did net bind the 13 kd peptide but for which an argument could be made for binding Group B octapeptides (opened bars).
Figure 2B:
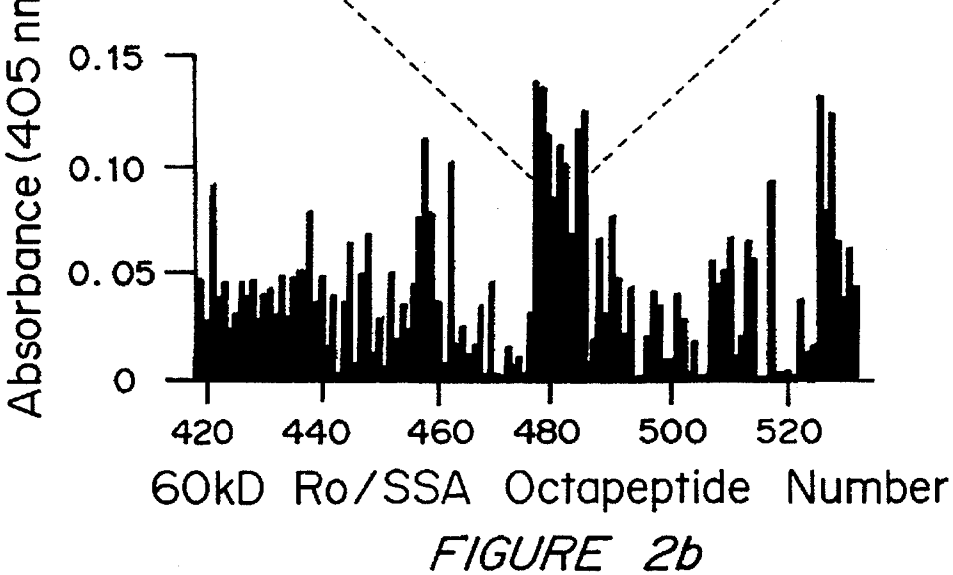
Figure 2A:
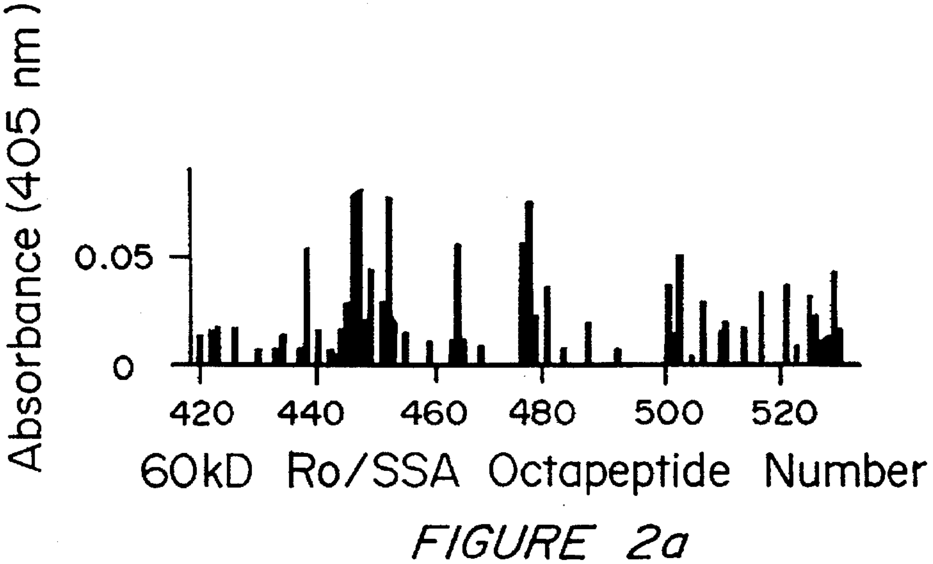

The reference sera bound one group of six consecutive octamers spanning the amino acid residue positions 480–494 which had marked reactivity above that of both normal serum and other surrounding octamers, as shown in FIG. 1. The corresponding sequence A I A L R E Y R K K M D I P A (SEQ ID No. 2) is predicted to contain an antigenic site and to have a high likelihood of being on the surface of the Ro/SSA 60 kD molecule. Major reactivity also resided in these and neighboring amino acids in seven additional anti-Ro/SSA positive sera identifying the 13 kD peptide in Western blots (FIG. 2). This region has the second highest antigenic index in the 119 amino acid sequence, as determined by the algorithm of Jameson and Wolff. *CABIOS* 4:181–187 (1988)(FIG. 1).

FIG. 2 presents the log average with respect to binding carboxyl terminal 112 overlapping octapeptides of eight anti-Ro/SSA patients who are positive in Western blot for binding to the 13 kDd peptide of Ro/SSA in Panel A. Panel B presents patients who are negative for binding the 13 kD peptide. There are three groups of octapeptides that appear to be substantially more reactive in the sera which bind the 13 kD peptide. They are octapeptides beginning at residues 457 through 462 (Group A), residues 477 through 485 (Group B), and residues 525 through 527 (Group C). These contain sequences T N T P A D V F I V F T D (SEQ ID No. 3), V H P A I A L R E Y R K K M D I (SEQ ID No. 4), and A L D V I R N F T L (SEQ ID No. 5), respectively. Group A was identified by three, Group B by seven, and Group C by four of the eight 13 kD binding anti-Ro/SSA sera tested. Panel C shows the maximum reactivity of the eight sera which bound the 13 kD peptide (shaded bars) and the two sera which did not bind the 13 kD peptide but for which an argument could be made for binding Group B octapeptides (opened bars). Note that the octapeptide of maximal binding for individual serum (Panel C) is more than twice the binding of the log averages (Panel A) for the anti-13 kD Western immunoblot positive sera. Nevertheless, the potential to most clearly reflect binding to the 13 kD Ro/SSA peptide appears to be found in the octapeptides spanning residues 477 and 492.

To determine whether binding observed in the region between amino acid residue 477 to 492 represents specific antibody and, more particularly, anti-Ro/SSA autoantibody binding, inhibition experiments were performed using synthesized peptide and affinity purified bovine Ro/SSA antigen. The reference serum maximally bound at the octapeptide beginning at amino acid residue number 485 and had the sequence E Y R K K M D I (SEQ ID No. 6). A number of pins were prepared with this sequence. Standard techniques were used to prepare a peptide containing this sequence, C A L R E Y K K M D I P A (SEQ ID. No. 7), and two control peptides, (Table I). The peptide containing E Y R R K M D I (SEQ. ID No. 6) sequence inhibited binding of antibody to the solid phase while those without the E Y R K K M D I sequence did not. Similarly, Ro/SSA antigen inhibited binding of antibody in the reference anti-Ro/SSA serum to E Y R K K M D I while bovine serum albumin did not. Together, these results establish that binding to E Y R K K M D I is specific and that this antibody is part of the anti-Ro/SSA population of antibodies.

There are differences between the human Ro/SSA antigen sequences that have been published by Deutscher, et at., *Proc. Natl. Acad. Sci. USA* 85:9479–9483 (1988) and Ben-Chetrit, et at., *J. Clin. Invest.* 83:1293–1298 (1988). These differences were also explored in eight of the anti-Ro/SSA sera. One of these bound to octapeptides which are unique to the carboxyl terminus of the 60 kD sequence published by Ben-Chetrit, et al.

antibody binding. Clearly, epitopes may be small since the alteration of a single amino acid in an antigen is often sufficient to substantially decrease binding, as demonstrated by Reichlin, M., *Immunochemistry* 11:21–27 (1974); Benjamin, D. C., et al., *Ann. Rev, Immunol.* 2:67–101 (1984); and Geysen, J. M., et al., *Proc. Acad. Sci. USA* 81:3998 (1984).

To assess whether structural similarity, as measured by quadrapeptide homology, is related to the antigenicity of Ro/SSA, an algorithm was derived to estimate the probability of there being an association between antigenicity and homology, referred to below as the Antigenicity Alignment Probability. First, the central octapeptide of each epitope was chosen following the application of simple rules. Only octapeptides bound by the anti-Ro/SSA reference serum with an absorbance greater than 1.0 could become the central antigenic octapeptide for an epitope. One central antigenic octapeptide was chosen from amongst multiple neighboring octapeptides with an absorbance greater than 1.0 when all octapeptides showed at least quadrapeptide homology. Octapeptides developing an absorbance less than 1.0 were taken into account only when an otherwise equivalent choice was required between candidates for the central antigenic octapeptide. Then, the octapeptide with the greatest near neighbor octapeptide binding by the anti-Ro/SSA serum was chosen.

TABLE I

Inhibition of binding to E Y K K M D I by preincubation of an anti-Ro/SSA serum with Ro/SSA antigen or with soluble synthesized peptide.

| Preincubation conditions for anti-Ro/SSA reference sera | Absorbance (O.D. at 405 nm) | Inhibition (%) |
|---|---|---|
| None | 0.700 | 0 |
| Ro/SSA (10 mcg/ml) | 0.220 | 68 |
| Ro/SSA (100 mcg/ml) | 0.109 | 84 |
| Albumin (10 mcg/ml) | 0.710 | 0 |
| C A L R E Y R K K M D I P A | 0.136 | 80 |
| E K Q I A N S Q D G Y V W Q V T D (Seq. ID No. 8) | 0.680 | 3 |
| Y K G E W K P Q I D N P D Y K G T (Seq. ID No. 9) | 0.706 | 0 |
| E D K E E D E E E D V P G Q A K D E L (Seq. ID No. 10) | 0.694 | 1 |

A representative experiment is as follows. A $10^{-2}$ dilution of anti-Ro/SSA reference serum was preincubated with bovine Ro/SSA or bovine serum albumin at the concentration indicated above or with one of four peptides at 10 mcg/ml before being incubated with polyethylene rods containing covalently bound E Y R R K M D I (SEQ ID No. 10) peptide. The extent of antibody binding was monitored at 405 nm and was detected with an anti-human gamma chain specific conjugate to alkaline phosphatase and an appropriate substrate, in this case, p-nitrophenylphosphate. The sequence bound to the solid phase rods, E Y R K K M D I (SEQ ID No. 1), is underlined in the synthesized soluble peptide containing the sequence from 480 to 492 of the 60 kD Ro/SSA peptide.

EXAMPLE 2

Relationship between the 60 kD Ro/SSA peptide and the nucleocapsid protein of the Indiana strain of vesicular stomatitis virus (VSV)

The octapeptide beginning at amino acid residue 485, EYRKKMDI, had the greatest antigenicity with the reference anti-Ro/SSA serum in the carboxy terminal 13 kD fragment of Ro/SSA (FIG. 1). A search of the National Biomedical Research Foundation (NBRF) protein sequence bank found the sequence EYRKKLMD (SEQ ID No. 11) in the nucleocapsid (N) protein of the Indiana strain of vesicular stomatitis virus which with the inclusion of a gap (*) in the Ro/SSA sequence of EYRKK*MD (SEQ ID No. 12) has very close homology.

Figure 3:
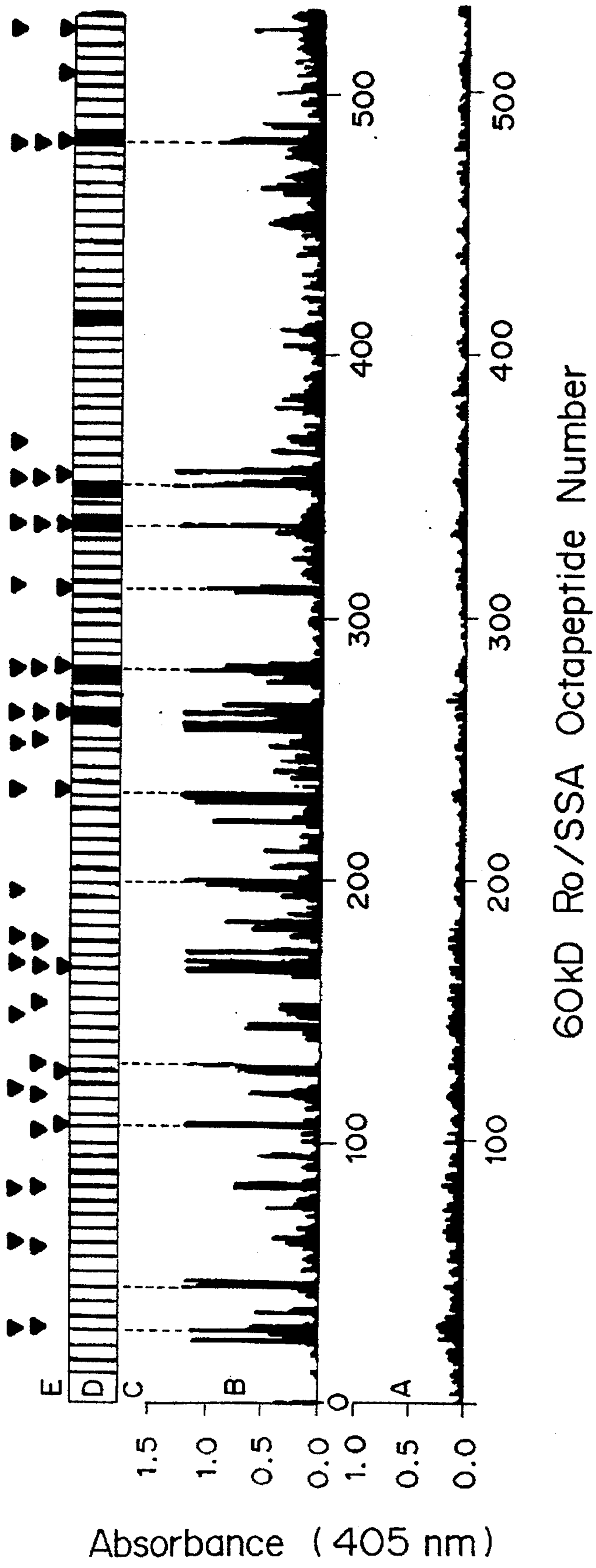
FIG. 3 is an analysis of binding of a human anti-Ro/SSA reference serum to overlapping octapeptides of Ro/SSA. Every possible octapeptide from the human 60-kDa Ro/SSA amino acid sequence has been synthesized onto a solid-phase support. An enzyme-linked immunosorbent assay has been (used to detect binding by human antibody. Octapeptide numbers indicate the sequence position of their amino-terminal amino acid and (A) Binding of a normal control serum. (B) Binding of the reference anti-Ro/SSA serum. (C) Central antigenic octapeptides are identified by broken lines. (D) Solid blocks indicate tetrapeptide and longer regions of the Ro/SSA sequence shared with the N protein of the Indiana serotype and average 5.5 octapeptides since there are three tetrapeptide and three pentapeptide identities. The remainder of the Ro/SSA sequence is arbitrarily partitioned into groups with an average size of 5.5 octapeptides (open blocks). All groups are continuous except the remainder octapeptides, which have been collected together from different parts of the sequence. (E) The central antigenic octapeptides from three additional anti-Ro/SSA precipitin-positive sera are indicated by ▼.
Figure 4:
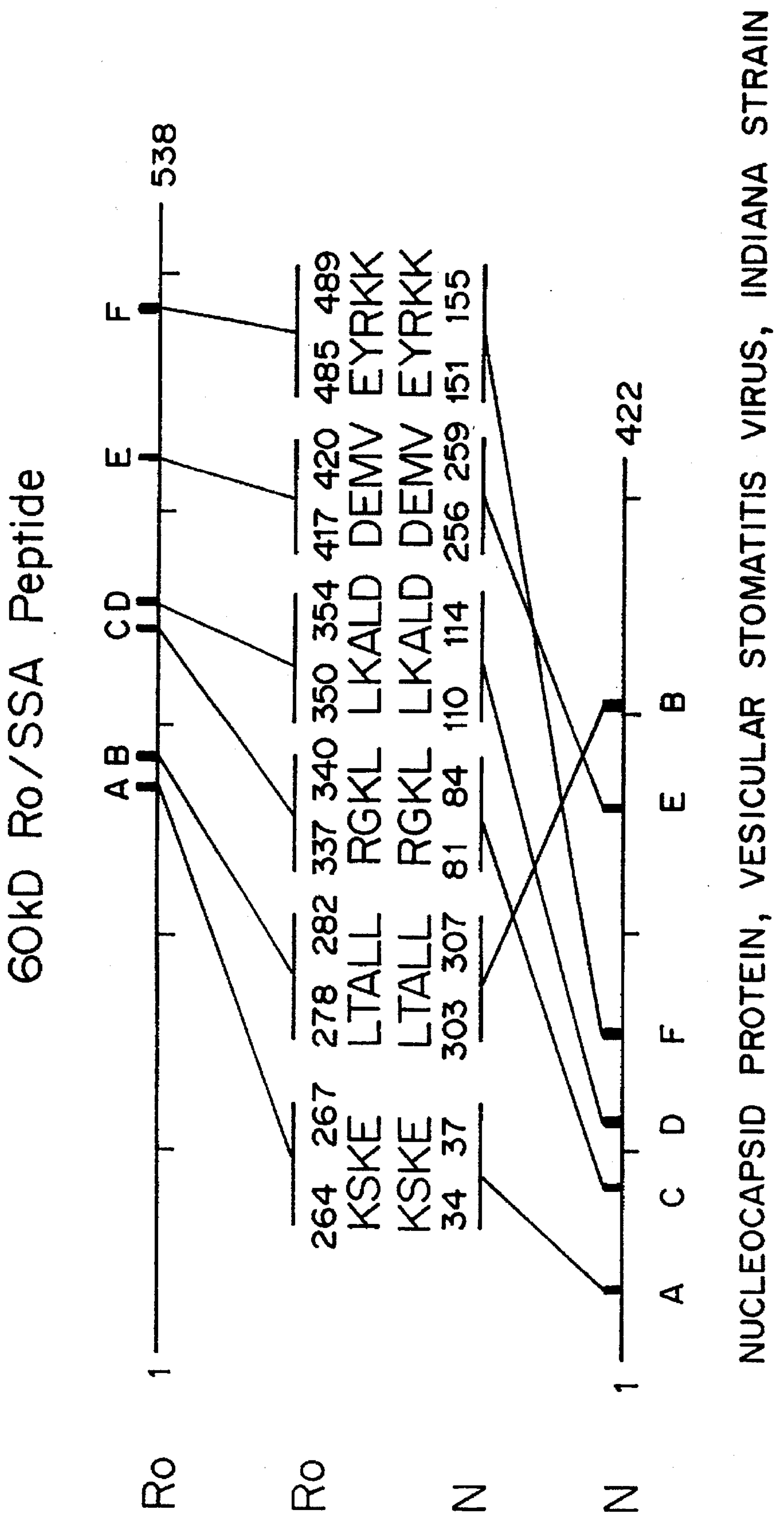
FIG. 4 shows the homologous regions of four or more amino acids between the human 60 kD Ro/SSA protein and the nucleocapsid (N) protein of the Indiana strain of vesicular stomatitis virus. Homologous regions are labeled in their order on the Ro/SSA sequence. Sequence positions of the homologous regions are demonstrated on Ro/SSA and the N protein. The standard single letter code is presented for amino acids in the homologous regions.

It was reasoned that if homology between N and Ro/SSA was reflected in one antigenic site, then other sites of Ro/SSA antigenicity might be related to homology between N and Ro/SSA. Six regions of at least quadrapeptide homology were shown to be shared between N and Ro/SSA (FIG. 4). A quadrapeptide level of homology was initially chosen since this should be sufficiently infrequent to be important from the perspective of the number of comparisons made and yet be large enough to be of potential importance for Following selection of the central octapeptide of each epitope, the octapeptides of the Ro/SSA molecule were organized into groups based upon the presence or absence of homology with N. A threshold of at least quadrapeptide homology was required for an individual octapeptide to be included in a group of Ro/SSA octapeptides all with this level of homology to N. By these criteria, there were six groups of Ro/SSA octapeptides with homology to N. Each member of these octapeptide groups had quadrapeptide homology between N and Ro/SSA and are identified by the solid areas in FIG. 3. The remainder of the molecule was arbitrarily divided into groups of octapeptides of essentially the same average size. No Ro/SSA octapeptide member of any of these latter groups had quadrapeptide homology with N.

A contingency table was developed by assigning each group of Ro/SSA octapeptides to one of four categories based upon the presence or absence of homology between N and Ro/SSA and upon whether or not the group contained an octapeptide that had previously been identified as a central antigenic octapeptide. In one example, five of the six octapeptide groups of Ro/SSA which shared quadrapeptide homology with N also contained a central antigenic peptide.

In another example, only nine of the ninety octapeptide groups which had no quadrapeptide homology with N contained a central antigenic peptide. The Antigenic Alignment Probability for the epitopes of Ro/SSA and its homology with N is 0.00017; meaning that such a relationship would be expected only once every 5,900 such comparisons. The odds ratio of 45 with a 95% confidence interval of 4.7 to 426 also supports there being a strong relationship. There is, therefore, a powerful association between the autoimmunity of Ro/SSA and the structure of the N protein of vesicular stomatitis virus. These are the first data suggesting that different areas of sequential antigenicity may be related to multiple areas of short sequence homology between an autoantigen and a foreign protein.

A number of probability arguments can be made that the sequence homology between Ro/SSA and N is related to the autoantigenicity of Ro/SSA. In addition to the Antigenic Alignment Probability (p<0.0002), the seven of eight match of EYRKK*MD (SEQ ID No. 12) of RO/SSA with EYRKKLMD (SEQ ID No. 11) of N is by itself very unlikely. If a random partitioning of the twenty amino acids and a random distribution of amino acids within sequences is assumed, then a probability of $6 \times 10^{-9}$ can be estimated. Since there are 3,318,616 octapeptides in the NBRF data base, one would expect to find an average of two matches at the seven of eight level for a specific query sequence every hundred times a data base of this size is searched. With these assumptions in addition to considering overlapping quadrapeptides as independent, the likelihood of finding two proteins the size of Ro/SSA and the N protein with at least the quadrapeptide homologies presented in FIG. 4 would be expected by a Poisson distribution in less than one of every 50,000 pairwise comparisons.

The number of available sequences is now large enough so the conclusions and assumptions underlying a relationship discovered on the basis of homology may be directly appraised by simulation experiments. To determine how unusual the level of homology observed between Ro/SSA and N is, every protein in the entire NBRF data base was assessed for quadrapeptide homology to Ro/SSA. Every area of quadrapeptide homology was included in the comparison and normalized for every 100 amino acids of Ro/SSA and of the query protein. If all overlapping quadrapeptides are independent, then Ro/SSA and N achieve a specific homology score of 0.401 (Table II). Homology at this level was unexpectedly common since there were 309 protein sequences or 2.5% of the NBRF data base with a greater homology score. Certainly, homologies at the density found between N and Ro/SSA are much more frequent than one in 50,000 as estimated above. The assumptions commonly made for probability estimates concerning the equal partitioning or random distribution of amino acids must, therefore, be wrong.

The central issue is whether or not antigenicity of Ro/SSA is more closely related to homologies between Ro/SSA and another sequence in the data bank rather than that already identified between Ro/SSA and N. The simulation experiments have been extended to calculate the Antigenicity Alignment Probability for all 12,476 protein sequences in the NBRF data base as shown in Table II. A number of sequences are shown to have a potentially important association between homology and antigenicity; sixteen have Antigenicity Alignment Probabilities less than 0.01 (Table II). For every one thousand tested, 1.3 sequences achieve this level of probability. Nevertheless, of the 12,476 protein sequences, the N protein of vesicular stomatitis virus remains the most closely related to the autoantigenicity of Ro/SSA. Comparisons are made in Table II.

TABLE II

| | | | |
|---|---|---|---|
| Protein Sequences with Homology to 60 kD Ro/SSA that is Potentially Associated with Ro/SSA Autoantigenicity | | | |
| Antigenicity Alignment Probability (P) | Odds Ratio for AAP | Homology Score | Protein (species-strain)- NBRF Access Code |
| 0.00017 | 45 | 0.401 | Nucleoprotein (vesicular stomatitis virus-Indiana)-vhvnn |
| 0.0012 | 32 | 0.312 | Nucleoprotein (vesicular stomatitis virus-Indiana)-vhvnv4 |
| 0.0036 | 18 | 0.173 | Ribonucleoside diphosphate reductase (E. coli)-s00926 |
| 0.0053 | 11 | 0.614 | Thymidylate kinase (S. cerevisiae)-kibyt8 |
| 0.0053 | 11 | 0.696 | Thymidylate kinase (S. cerevisiae)-a26127 |
| 0.0053 | 11 | 0.201 | Probable glycoprotein H (H. zoster)-vgbe37 |
| 0.0062 | 22 | 0.197 | Interferon-induced 56 kD protein (H. sapien)-a25407 |
| 0.0068 | 27 | 0.541 | Histone H2A.vD (D. melanogaster)-s01234 |
| 0.0068 | 24 | 0.150 | Cytochrome p450 III(A4) (O. cuniculus)-a29487 |
| 0.0068 | 24 | 0.073 | RAD2 protein (S. cerevisiae)-a29839 |
| 0.0068 | 24 | 0.190 | Achaete-scute locus protein T8 (D. melanogaster)-s01166 |
| 0.0078 | 22 | 0.785 | Histone H2B (C. elegans)-hskw22 |
| 0.0078 | 22 | 0.211 | Cytochrome P450 PB-1(ps) (R. norvegicus)-a28516 |
| 0.0078 | 22 | 0.372 | Heat-labile enterotoxin A chain precursor (E. coli)-gleca |
| 0.0087 | 11 | 0.121 | Pol polyprotein (D. melanogaster)- |

TABLE II-continued

| Protein Sequences with Homology to 60 kD Ro/SSA that is Potentially Associated with Ro/SSA Autoantigenicity | | | |
|---|---|---|---|
| Antigenicity Alignment Probability (P) | Odds Ratio for AAP | Homology Score | Protein (species-strain)-NBRF Access Code |
| | | | gnft42 |
| 0.0090 | 22 | 0.115 | C1-tetrahydrofolate synthase precursor (*S. cerevisiae*)-a28174 |
| 0.0097 | 10 | 0.202 | Transforming protein precursor (*H. sapien*)-tvhudb |

The Antigenicity Alignment Probability is calculated from a one-tailed Fisher's exact test of the categorical distribution of the central antigenic octapeptides upon the groups of octapeptides of the Ro/SSA sequence organized according to the presence or absence of quadrapeptide homology. The Odds Ratio for AAP (Antigenicity Alignment Probability) is the odds ratio of the resulting contingency table. The Homology Score is a measure of overlapping quadrapeptide similarity between Ro/SSA and the query protein. It is calculated for each region of homology as X-3 where X is the number of amino acids with exact homology and then expressed as the density of overlapping quadrapeptide homologies per 100 amino acids of Ro/SSA and of the query sequence.

Vesicular Stomatitis Virus

Vesicular stomatitis virus is the prototype of the Vesiculovirus genera, and both New Jersey and the Indiana strains are in common laboratory use. The N proteins from the two strains are 80% homologous at the amino acid level, as reported by Gallione, C. J., et al., *J. Virol.* 39:529–535 (1981); and Banerjee, A. K., et at., *Virology* 137:432–438 (1984). The differences are sufficient, however, to dramatically alter the alignment of homology with antigenicity. Only three areas of quadrapeptide homology exist between the New Jersey N protein and Ro/SSA and of these, only one identifies an antigenic octapeptide of Ro/SSA. The Antigenicity Alignment Probability, calculated as in Table II, for homology of Ro/SSA with N protein of the New Jersey strain being associated with Ro/SSA autoantigenicity is 0.95. This is dramatically different than the result obtained with the Indiana strain N protein. The New Jersey strain is, therefore, not likely to be the most closely related to the candidate viral agent.

Two Indiana strain N protein sequences are available which vary by only three amino acids, as described by Gallione, C. J., et at., *J. Virol.* 39:529–535 (1981); and DePolo, N. J., et at., *J. Virol.* 61:454–464 (1987). One of these changes is found in an area where homology and antigenicity would otherwise coincide and, hence, the Antigenicity Alignment Probability is adversely affected (Table II and FIG. 5). Despite the elimination of a site of homology, this protein sequence achieves the second most significant Antigenicity Alignment Probability of the sequences in the data base (Table The amino acid sequence of the Indiana strain in the near neighborhood of identical homology with Ro/SSA (FIG. 5) provides additional evidence that this strain must be very closely related to the candidate virus. The inclusion of single amino acid gaps in the Ro/SSA sequence increases the homology between Indiana N and Ro/SSA as seen in FIG. 5. In each instance, the gap is found in the Ro/SSA sequence on the carboxy side of an area of quadrapeptide or pentapeptide homology with Ro/SSA. Each of the three regions with near neighborhood homology with the Indiana strain are antigenic. The rabies virus N protein has no such near neighbor homology. Such similarity is present in the New Jersey strain homologies, but neither of the two regions is antigenic. Indeed, of the 35 proteins with the most significant Antigenicity Alignment Probability, none had as many near neighbor homologies with Ro/SSA in antigenic regions for anti-Ro/SSA as did the N protein ($p<0.015$ by the Poisson distribution for the five amino acids involved in near neighbor homologies of the Indian strain N protein (FIG. 5)). This result means that N is exceptional, even of the set of proteins with a possible structural association between homology and antigenicity. Beyond the identical homologies considered in the Antigenicity Alignment Probability (Table II), this is additional structural information which further suggests a relationship between N and Ro/SSA autoantigenicity.

Many features of vesicular stomatitis virus are consistent with those of a potential etiologic agent of the anti-Ro/SSA associated rheumatic autoimmune diseases. The vesicular stomatitis virus leader sequence binds La/SSB, and the earliest known effect of vesicular stomatitis virus infection upon cellular metabolism is the inhibition of U particle assembly, as reported by Kurilla, M. G., et al., *Cell* 34:837–845 (1983); Fresco, L. D., et at., *Mol. Cell Biol.* 7:1148–1155 (1987); and Crone, D. E., et at., *J. Virol.* 63:4172–4180 (1989). La/SSB and the U particles are common autoantigens in systemic lupus erythematosus, as reported by Harley, J. B., et al., *Rheumatic Disease Clinics of North America: Systemic Lupus Erythematosus* 14(1): 43–56 (1988). Vesicular stomatitis virus infects cells through nonspecific glycoproteins. Consequently, the virus has a tremendous host range, even with isolates from plants growing well in mammalian tissue culture cells, as described by Superti, F., et at., *J. Gen. Virol.* 68:387–399 (1987). A variety of human tissues would also be expected to support the viral infection, perhaps reflecting the clinical heterogeneity of SLE and Sjorgren's syndrome. Vesicular stomatitis virus has improved survival in complement deficient serum which is consistent with the observation that many complement component deficiency states predispose to SLE, reviewed by Beebe, D. P., et al., *J. Immunol.* 126:1562–1568 (1981); Agnello, V., in *Systemic Lupus Erythematosus*, pp. 565–589 (John Wiley and Sons, New York 1987). Patients with SLE produce very high levels of interferon which induces latency of vesicular stomatitis virus. Interferon inhibits the production of intact virions which could explain the inability to find assembled viral particles of any origin in patient tissues, as reported by Prebie, O. T., et al., *Science* 216:429–431 (1982); Bishop, D. H. L., *Rhabdoviruses pp.* 69–98 (CRC Press, Boca Raton, Fla. 1980). During latency, viral antigens are expressed on cell surfaces, which may constitute a source of continuing antigenic stimulation.

An alternative model of disease in which the specific autoantibodies produced are a consequence of a general defect should also be considered. The N protein and vesicular stomatitis virus would accordingly only be related to anti-Ro-SSA autoantibodies. Other viruses or foreign antigens would serve as stimuli or immunogens for other observed autoantibodies and other autoimmune disease related phenomena within the context of the general defect.

There have been no reports of vesicular stomatitis infection of livestock in Europe. Since the anti-Ro-SSA associated human diseases occur in Europe as well as in North America, the Indiana strain of vesicular stomatitis virus may not itself be involved with the anti-Ro-SSA autoimmune response. There are, however, over thirty known strains of related rhabdoviruses; for most, the global distribution is unknown, as reported by Bishop, D. H. L., Rhabdoviruses, Vol. 1, pp. 1–22 (CRC Press, Boca Raton, Fla. 1979).

Analysis of tripeptide homology between N protein and Ro-SSA

As a trial of the robustness of the overall method, the Antigenic Alignment Probability was revised for the case of tripeptide homology between N and Ro/SSA. Antigenicity was defined by central antigenic octapeptide binding by the reference anti-Ro/SSA serum as presented in FIG. 3. Eight of the twenty-seven areas in Ro/SSA which had at least tripeptide homology with N were antigenic while only six of the fifty-two areas with no tripeptide homology were antigenic. Therefore, the Antigenic Alignment was 0.048 with an odds ratio of 3.2. This is a much weaker association than was found at the quadrapeptide level but nevertheless remains significant. Consequently, these data support a specific autoimmune relationship between N and Ro/SSA even at the level of tripeptide homology where the number of antigenically irrelevant homologies may be increased.

Other Anti-Ro/SSA Sera.

The antigenicities of a total of six anti-Ro/SSA sera were evaluated for binding to the 531 octapeptides of Ro/SSA. Two sera which formed a precipitate with purified native 60-kDa Ro/SSA but did not convincingly bind 60-kDa Ro/SSA in immunoblots did not bind any of the Ro/SSA octapeptides above background. Presumably, the anti-Ro/SSA autoantibodies of these sera bind only conformational epitopes. Sera with similar behavior have previously been described in an immunoblot analysis by James, et al., *Arthritis Rheum.* 33:102–106 (1990), and in the experiments analyzing the fine specificity of the 13-kDa carboxyl terminus of Ro/SSA. The other sera bound an approximate subset of the epitopes bound by the reference serum as presented in FIG. 3. The positions of the central antigenic peptides for these sera are indicated in FIG. 3E. With the Indiana serotype N sequence (V H V N N SEQ ID No. 13), these sera produced antigenicity alignment probabilities of 0.0013, 0.0048, and 0.0081. None of these sera bound the octapeptides containing the shared pentapeptide L K A L D (SEQ ID No. 20). Since this pentapeptide was not shared with the second Indiana strain N protein sequence [VSV-IND#2 in FIG. 5 (V H V N 4)] the antigenic alignment probabilities were higher with this N protein sequence: 0.00040, 0.00016, and 0.0027, respectively. While some anti-Ro/SSA Ro/SSA sera do not appear to bind the linear sequence, in many others the sequential autoantigenicity of Ro/SSA is related to the sequence similarity of Ro/SSA with an N protein of vesicular stomatitis virus.

EXAMPLE 3

Application of the method of identifying an etiologic or potential immunogen for the La/SSB and nRNP autoantigens.

Anti-Ro/SSA autoantibodies have been associated with other autoantibodies including an anti-La/SSB. The gene for La/SSB has been cloned and the protein sequenced, as reported by Chambers and Keene, *J. Biol. Chem.* 263:18043–18051 (1988). When one compares the sequence of the most active octapeptide which spans the amino acid position 485 to 492 with the known sequence of La/SSB, there are no closely related sequences. However, La/SSB, against which autoantibodies are made in approximately a third of the anti-Ro/SSA precipitin positive patients, binds the vesicular stomatitis virus leader sequence. The VSV matrix (M) protein contained short sequence homology to La/SSB in three positions which included residues 315–318(L K K I SEQ ID No. 14), 337–342(K G K G K G SEQ ID No. 15), and 351–354(G K G K SEQ ID No. 16).

The U1 nRNP 68KD antigen has also been compared to the proteins of the vesicular stomatitis virus, both Indiana and New Jersey strain. The U1 68KD protein is the major autoantigen to which the anti-nRNP autoantibodies are directed. Anti-nRNP antibodies are found in about 40% of patients with SLE. This autoantigen has been found to have homology with the M protein of the vesicular stomatitis virus, Indiana strain. This is the same viral protein which shares homologous regions with La/SSB; however, no individual sequence has homology of four or greater amino acids shared among all three proteins. Overlapping oligopeptides spanning the U1 68KD protein sequence will be synthesized and a search against the known protein sequences will be conducted as has been done for Ro/SSB. The data that these autoantigens share multiple short homologies with a vesicular stomatitis virus protein reinforces the idea of vesicular stomatitis virus as a potential etiologic agent in autoimmune diseases. Furthermore, data such as that obtained for Ro/SSA and La/SSB concerning the coincidence of antigenicity and multiple site molecular mimicry will be of interest.

EXAMPLE 4

Testing of antigenic agents homologous to Ro/SSA as an etiologic agent of autoimmune disease Anti-Ro/SSA autoantibodies are not only common in systemic lupus erythematosus and Sjogren's syndrome (SS), but may also have a pathogenic role in congenital complete heart block and neonatal lupus dermatitis. Mothers of young children, less than ten years old, and mothers of male lupus children have unexpectedly elevated levels of anti-Ro/SSA compared to the other primary relatives, as reported by T. J. A. Lehman, et al., *Arthritis Rheum.* 32, 1414–1420 (1989). These observations along with immunochemical evidence showing an antigenic relationship of Ro/SSA to a viral structural protein (discussed in example 3) led to the hypothesis that a specific viral infection in an appropriately susceptible host leads to anti-Ro/SSA autoantibodies.

The data in examples 1 to 3 demonstrate that an antigenic link has been found between the autoantigen Ro/SSA and the nucleocupsid (N) protein of the Indiana strain of vesicular stomatitis virus (VSV). This is a rhabdovirus, all known species of which have a similar organization of five proteins. Four N protein sequences for rhabdoviruses have been obtained by Gallione, et al., *J. Virol.* 39:529–535 (1981), DePolo, et al., *J. Virol.* 61:454–464 (1987) and Banerjee, et al., *Virology* 137:432–438 (1984). The rabies virus N protein is the most distant from the Indiana strain virus and the two N proteins have only 40 percent homology at the amino acid level. The rabies virus N protein sequence has three quadrapeptides homologous with 60 kD Ro/SSA (FIG. 5), none of which were found in an antigenic region of Ro/SSA. The New Jersey strain is serologically distinct from the Indiana strain of-vesicular stomatitis virus, as reported by Frazier and Shope, Serologic relationships of animal rhabdoviruses, as reported by Bishop, D. H. L., *Rhabdoviruses* pp. 43–64 (CRC Press, Boca Raton, Fla. 1979), but the two viruses are closely related. The two N proteins have 60 percent homology at the amino acid level. These changes, however, are sufficient to substantially alter the homologies with 60 kD Ro/SSA (FIG. 5). The relationship between antigenicity of Ro/SSA and the homologies with the New Jersey strain N protein are substantially weaker than those found with the Indiana strain N protein sequence.

It is hypothesized that an infection by a rhabdovirus relative of the Indiana strain of the vesicular stomatitis virus is important in the development of anti-Ro/SSA autoantibodies. Commercially available anti-vesicular stomatitis ascites raised in a mouse was tested for binding to bovine Ro/SSA, La/SSB, and nRNP. Relative to a control mouse ascites, the anti-vesicular stomatitis virus clearly bound bovine Ro/SSA in a solid phase ELISA. Therefore, this experiment serves to partially confirm this hypothesis for a heteroimmune system.

To determine which rhabdovirus may be the etiologic or immunogenic agent, first, the overlapping octapeptides of 60 kD Ro/SSA and the vesicular stomatitis N protein can be constructed and tested for antibody in childhood systemic lupus erythematosus (SLE) proband and controls. From the hypothesis, one would predict that antibodies to areas of structural similarity between Ro/SSA and the N protein might predominate in the early anti-Ro/SSA autoimmune response and the antibodies to the other regions of N protein would have the greatest likelihood of still being present in the early anti-Ro/SSA autoimmune response. Second, these same antigenic properties of the N protein may be found in the mothers of younger children and male children with lupus, consistent with the possibility of a congenital or childhood infection being an important factor in the subsequent disease of these patients. Third, various rhabdovirus strains can be tested for antigenicity. Those which have proteins reactive with anti-Ro/SSA autoantisera in addition to the N protein can be tested in the pedigrees available by Western immunoblot.

As early as 1967, viruses were suspected as a cause of SLE based on observations in NZB mice (Mellors, R. C. and Huang, C. Y. *J. Exp. Med.* 126:53–62 (1967)). A number of early findings suggested a viral etiology in human SLE. These included elevated anti-viral antibody titers (Phillips, P. E. and Christian, C. L. *Science* 168:982–984 (1970)), elevated interferon levels (Preble, O. T., et al., *Science* 216:429–431 (1982)), and inclusion bodies in diseased kidneys (Fresco, R. *Fed. Proc.* 27:246 (1968) (Abstract)). Eventually, all these findings have been purported to be non-specific (Levy, J. A. *Science* 182:1151–1153 (1973); Phillips, P. E. and Christian, C. L.: Infectious agents in chronic rheumatic diseases. In Arthritis and Allied Conditions, 9th ed. McCarty, D. J., ed. pp 320–328 (Lea and Febiger, Philadelphia 1979)) or not reproducible (Russell, P. J., et at., *Clin. Exp. Immunol.* 6:227–239 (1970); Schaap, O. L., et at., *Pathol. Microbiol.* 42:171–174 (1975)).

In recent years, cytomegalovirus (CMV), Epstein-Barr virus (EBV), and retroviruses have been most often implicated in the pathogenesis of both SLE and Sjogren's syndrome. Seroepidemiologic evidence for an association of EBV or retrovirus with SLE or SS has been presented, but other studies have been reported which have not found evidence implicating these viruses in rheumatic diseases.

The mechanism by which putative agent(s) might provoke an autoimmune response and subsequent disease are several. Molecular mimicry in which antigens from the pathogen cross react with self components is one such mechanism. In rheumatic heart disease and Chagas disease, molecular mimicry has been shown to occur. As yet, no pathogen has previously been shown to have such a molecular relationship in SLE or SS. The data shown above supports the proposal that molecular mimicry and immunoreactivity between rhabdovirus and the anti-Ro/SSA autoantibody response found in SLE play a role in the pathogenesis of the disease.

Additional support for the argument that rhabdoviruses should be considered as the etiologic agent of the anti-Ro/SSA associated autoimmune rheumatic diseases include the following: First, as noted above, La/SSB against which autoantibodies are made in almost half of the anti-Ro/SSA precipitin positive patients, binds the vesicular stomatitis leader sequence. Vesicular stomatitis virus also inhibits the assembly of the spiceosome particle, which is composed of the proteins to which the anti-RNP and anti-Sm responses are directed. Second, patients with early classical pathway complement component deficiencies tend to have a high incidence of SLE. Most of those who do have complement deficiency and SLE also have anti-Ro/SSA. Sera deficient in complement component C4 have reduced capacity to neutralize and clear virus. SLE patients have high levels of interferon. Vesicular stomatitis virus is sensitive to interferon in that lytic infection with formation of intact virions is inhibited in vitro and the virus infection becomes latent. Vesicular stomatitis virus has been documented to be latent in vivo for up to a year. Rhabdoviruses have a nonspecific mechanism for cellular attachment which means that they can infect many different tissues, perhaps contributing to the clinical heterogenicity of SLE.

Vesicular stomatitis virus does infect humans (Sekellick, M. J. and Marcus, P. I. Persistent infections of rhabdoviruses: in *Rhabdoviruses*, Vol. 1, Bishop, D. H. L., ed. pp. 67–98 (CRC Press, Boca Raton, 1980); Tesh, R. B., et al., *Am. J. Epidemiol.* 90:255–261 (1969); Tesh, R., et at., *Am. J. Trop. Med.* 26(2):299–306 (1977)). In areas where the virus is known to be epizoic, up to 90% of the human population shows serologic evidence of past infection. Epizoic areas include most of the Western hemisphere and parts of the Middle East; however, since vesicular stomatitis virus is not believed to have been found in Europe, it is unlikely that the Indiana strain of vesicular stomatitis virus itself is responsible for loss of tolerance to Ro/SSA. Nonetheless, as the prototype rhabdovirus, the Indiana strain of vesicular stomatitis virus has been well studied. There are approximately 30 rhabdoviruses known to infect humans, most of which have not been characterized. One of these or a virus yet to be isolated must be seriously considered as important etiologic agents leading to autoimmunity to Ro/SSA and the associated disease states.

Although a rhabdovirus relative of vesicular stomatitis virus may be important for the generation of anti-Ro/SSA autoantibodies in an individual who already has or is potentiated for SLE, the pathogenic agent may be separable from the factor that predisposes to or causes SLE. Accordingly, the anti-Ro/SSA negative SLE patients may have no immunologic evidence of prior exposure to a virus like vesicular stomatitis virus and one may not expect to find much in the way of Ro/SSA octapeptide binding from the Ro/SSA negative sera. Multiple mechanisms for the loss of tolerance to other autoantigens probably exist, but would seem to at least include a mechanism of molecular mimicry at multiple sites as described here for Ro/SSA. A variety of bacterial, viral or other environmental substances may influence the particular autoantibodies which develop. Under this model, the capacity to develop such autoantibodies would be the general deficiency leading to SLE, but each of the specific autoantibodies would have originated from a limited set of potential triggering antigens.

The second general model is that the rhabdovirus being sought is the etiologic agent for SLE. If so, then all SLE patients may, but are not required to, have evidence of N protein antigenicity demonstrated by octapeptide binding. The explanation for the presence of not only anti-nRNP and anti-Sm autoantibodies but also the myriad of other known autoantibody specificities in SLE would be the major enigma requiring explanation. Possibilities would include a similar relationship between the U peptides and a rhabdovirus protein as is herein described between Ro/SSA and N. Sequence comparison between the 68 kD U1 peptide and various rhabdovirus proteins has revealed homology with the M protein of Indiana strain at a level similar to that found between 60 kD Ro/SSA and the N protein. It owuld seem, however, that there are too many autoantibody specificities in SLE for this to constitute the entire explanation. If this second model is true, then the viral infection itself would need to modulate an immune cell regulatory population which would encourage the generation of autoantibodies.

To test these hypotheses, one can obtain a number of rhabdovirus strains and grow them on a selected cell line for subsequent purification. High-titer virus can be grown and purified as previously described by Clark, H. F., *Rhabdoviruses* pp. 23–42 (1980). Cloned vesicular stomatitis virus is added to monolayers of BHK-21, or other appropriate cell line. With an infectious innoculum, a general cytopathic effect is noted at about 24 hours. Supernatant is then harvested and subjected to sequential centrifugation at 1,000×g for 10 minutes, then 10,000×g for 10 minutes. Next, the virus is pelleted through a 50% glycerol cushion at 85,000×g for 90 minutes. The pellet is then suspended in a 10 mM Tris, 0.1M NaCl, and 0.001M EDTA (TNE) solution, and sonicated at 40 watts for 10 seconds. The virus is then layered on a 10% to 40% sucrose gradient and subjected to centrifugation at 50,000×g for 90 minutes. The visible band obtained is diluted in TNE solution and centrifugated again at 50,000×g for 90 minutes. The now purified virus is dialyzed against a Tris buffer overnight at 4° C. and can be stored at −70° C.

Antibody binding can be assessed by standard Western blotting strategy against a panel of sera. The virus isolate from which the N protein binds at least the anti-Ro/SSA precipitin positive patients and any of the four other rhabdovirus proteins in any SLE or appropriate control serum will be of great interest. This strategy exploits the potential for the extremely broad host range of rhabdoviruses to be relevant. For example, even the yellow lettuce virus is a rhabdovirus which infects and grows in mammalian cells.

EXAMPLE 5

Diagnostic Reagents and assays based on a VSV-like rhabodovirus

There are several embodiments of diagnostic reagents according to the present invention that can be used for diagnosis of autoimmune disorders, exposure to, or infection by, an etiologic or immunogenic agent, and vesicular stomatitis virus infection. First, anti-viral antibodies could be used to detect viral antigens in cell extracts or serum and bodily fluids. These antibody assays include assays such as sandwich ELISA assays, Western immunoblot, radioimmunoassays, and immunodiffusion assays. Techniques for preparing these reagents and method for use thereof are obvious to one skilled in the art.

It is possible that vesicular stomatitis virus persists as a latent infection in some patients. In these circumstances immunologic reagents could be used to detect the presence of particular viral antigens in tissue sections or on isolated cells using methodology familiar to one skilled in the art. Anti-viral antibody can be detected by using the anti-viral agents to trap viral antigens, as in a sandwich ELISA, using methods known to those skilled in the art.

Nucleotide or amino acid probes can be prepared based on the antigenic sequences identified in FIGS. 3 and 4 for either the Ro/SSA or the rhabdoviruses tested as described in example 5, such as the Indiana strain of VSV. These are labelled using dyes, or enzymatic, fluorescent, chemiluminescent, or radioactive labels which are largely commercially available. These probes can be used to screen sera or tissue samples from suspected patients or animals suspected of being reservoirs of the virus believed to be the etiological agent. For example, the appropriate viral sequences (or their complementary nucleic acid) could be marketed for use in en situ hybridization as a method to detect infection in specific tissues or peripheral blood cells. As a second example, nucleic acid primers could be prepared which with reverse transcriptase and the polymerase chain reaction could be used to expand viral sequences. Detection of the viral sequences may follow with specific nucleic acid probes, with electrophoresis of a fragment with a predicted size or with electrophoresis and restriction digestion with a particular restriction endonuclease.

EXAMPLE 6

Methods and compositions for treating an autoimmune disorder having a VSV-like rhabdovirus as the etiological agent Treatment with anti-viral agents alone or in combination with immunosuppressants.

At present, therapy for autoimmune diseases such as SLE is non-specific in that it cannot be directed at the underlying cause. Immunosuppressants which are currently in use include glucocorticoids, methotrexate, azathioprine, cyclophosphamide, non-steroidal antiinflammatory agents, antimalarials, and other non-specific therapeutics such as sun screens. Usage and dosage of these drugs is dictated by the disease manifestations. Glucocorticoids, for example, are used in high dosages to treat some neurologic complications of SLE. Both azathioprine and cyclophosphamide are used as an attempt to halt or reverse renal damage. Limiting side effects are common for all of the immunosuppressants. This generally relates to their non-specific effect on not only the portion of the immune system involved in SLE but also on the normally functioning, protective immune system. For example, the dose of cyclophosphamide is generally regulated, and limited, by toxicity to hematopoesis.

Based on the foregoing, it can be concluded that autoimmune disorders such as SLE are initiated by infection with a VSV-like rhabdovirus. Accordingly, patients could be treated not only by the immunosuppressants mentioned above but also by immunosuppressant compounds having non-specific antiviral activity, such as interferon, or inducers of interferon including fluorene, dibenzofuran, tilorone HCl, or bacterial lipopolysaccharide, or compounds having specific activity against vesicular stomatitis virus, alone or in combination with the immunosuppressants.

Immunosuppressants would also have the potential to be specific and be biological. For example, a protein containing the appropriate composition based upon the homology of N protein with Ro/SSA and antigenicity of Ro/SSA and N could act as an immunosuppressant for the anti-Ro/SSA response. This or another compound, for example, based upon complementary considerations may stimulate the anti-N protein (or other viral antigen) response and act to clear the virus infection from the affected patient. As another example, anti-sense DNA or RNA or derivatives thereof containing nucleic acid sequence related to VSV may inhibit the production of virus antigens and potentially eliminate viral infection.

Therapeutic compounds are generally administered in a pharmaceutically acceptable carder. Pharmaceutical carriers are known to those skilled in the art and include encapsulation of compounds for oral administration, for example, in an enteric coating or in combination with a binder such as stearate or lactose, or in solution. Acceptable solutions include sterile water, saline, and buffered solutions at physiological pH. Vaccines can be administered orally, intramuscularly or subcutaneously. Other compounds will be administered according to standard procedures used by those skilled in the art. As defined herein, a pharmaceutical carrier is usually inert by itself but may have biological activity. For example, a vaccine may consist of immunogenic peptides or proteins in combination with an adjuvant.

Treatment with peptides bound by autoantibodies to remove or neutralize the autoantibodies Alternatively, the agents used for treatment might include peptides homologous to the identified antigenic, molecular mimicry sequences. These peptides, either free or bound to a carder, could be delivered to a patient in order to decrease the amount of circulating antibody with a particular specificity. In addition, knowledge of the cross-reacting epitopes between a foreign antigen and an autoantigen, such as N and Ro/SSA, may allow for reinduction of tolerance. It is well known in experimental models of the immune response that the response can be suppressed and tolerance induced by treatment with the antigen. Peptide therapy with the cross-reacting sequences may be a potential therapy in autoimmune diseases.

Production of vaccines to prevent development of autoimmune disease based on the isolated etiologic or antigenic agent It may be possible to prevent SLE and related diseases by vaccination of populations at risk. Vaccination programs have been very successful in man for selected diseases (e.g. polio). Such a vaccine could be an attenuated or killed virus. A vaccine product could also be manipulated by recombinant DNA techniques so that the regions of antigenicity and homology in the autoantigen are altered, deleted or destroyed in the expressed immunogen. By stimulating the immune response to portions of the immunogen, the immune system may be able to eliminate the infection or reinduce an immune state of tolerance in the affected patient. The engrafted scid mouse model will be extremely useful in assessing the consequences of these biologics upon the patient's immune system.

Once the actual etiologic rhabdovirus is identified, many opportunities for affecting the outcome are possible. Since interferon is known to cause most rhabdoviruses to lose infectivity and become latent, one would not expect to be able to directly culture rhabdoviruses from tissues. There are, however, other methods available to define the virus. DNA primers based upon the N protein nucleic acid sequence and constructed from the areas of peptide homology between N and Ro/SSA could be used to expand rhabdovirus sequences from patient and normal specimens. Northern blots of mRNA from lymphocytes using available or constructed cDNA viral probes may reveal additional evidence of infection and provide the basis by which to recover and clone viral sequences.

It should be possible to use viral peptides, either produced by cleaving cultured virus or synthetically, using methods known to those skilled in the art, to create vaccines for that portion of the population at risk, to serve as neutralizing agents for the circulating autoantibodies, or to induce tolerance to epitope(s) of a foreign antigen or an autoantigen. The sequences preferably used for the vaccine are those portions of the viral proteins which are antigenic but not homologous to regions of the autoantigen. For example, the multiple homologous regions between the rhabdovirus proteins and self proteins that become autoantigens could be eliminated by recombinant DNA technology. A vaccine administered before the infection with the virus or at least before onset of the disease could prevent autoimmunity. Using this strategy, an individual would develop immune competence against the etiologic agent after vaccination with the manipulated virus. When challenged with the etiologic agent, an infection and the autoimmune consequences would be prevented.

Removal of autoantibodies from the patient using peptides of the antigenic or etiologic agent The amino acid sequences can also be used to make agents for neutralizing circulating antibodies or immobilized on substrates in extracorporeal devices for specific removal of autoantibodies, using methodology known to those skilled in the art.

EXAMPLE 7

Juxtaposition and lesser degrees of homology shuffling between autoantigens and other proteins In the instance of 60 kD, Ro/SSA and the N protein show that there may be many areas of homology between autoantigen and the alleged inciting protein. Based on the work presented above, one aspect that is suspected to be extremely important in how the autoimmune state is established is the relative rearrangement in the areas of homology between these molecules. For example, consider the scenario when an N protein is the original immunogen. Under these circumstances and according to what is generally accepted by those skilled in the art of immunology, the immune response to homologous region A (see FIG. 4) would be largely independent of the immune response to region B (FIG. 4). The potential for conflicting immune processing and regulatory signals are great when these two signals are brought much closer together in Ro/SSA. Perhaps their separation by only 11 bases in the Ro/SSA sequence is adequate to break tolerance to Ro/SSA and subsequently generate the intense autoimmune response seen in some patients. The C and D areas of homology are a second potential example of this phenomenon.

Figures 6A, 6B:
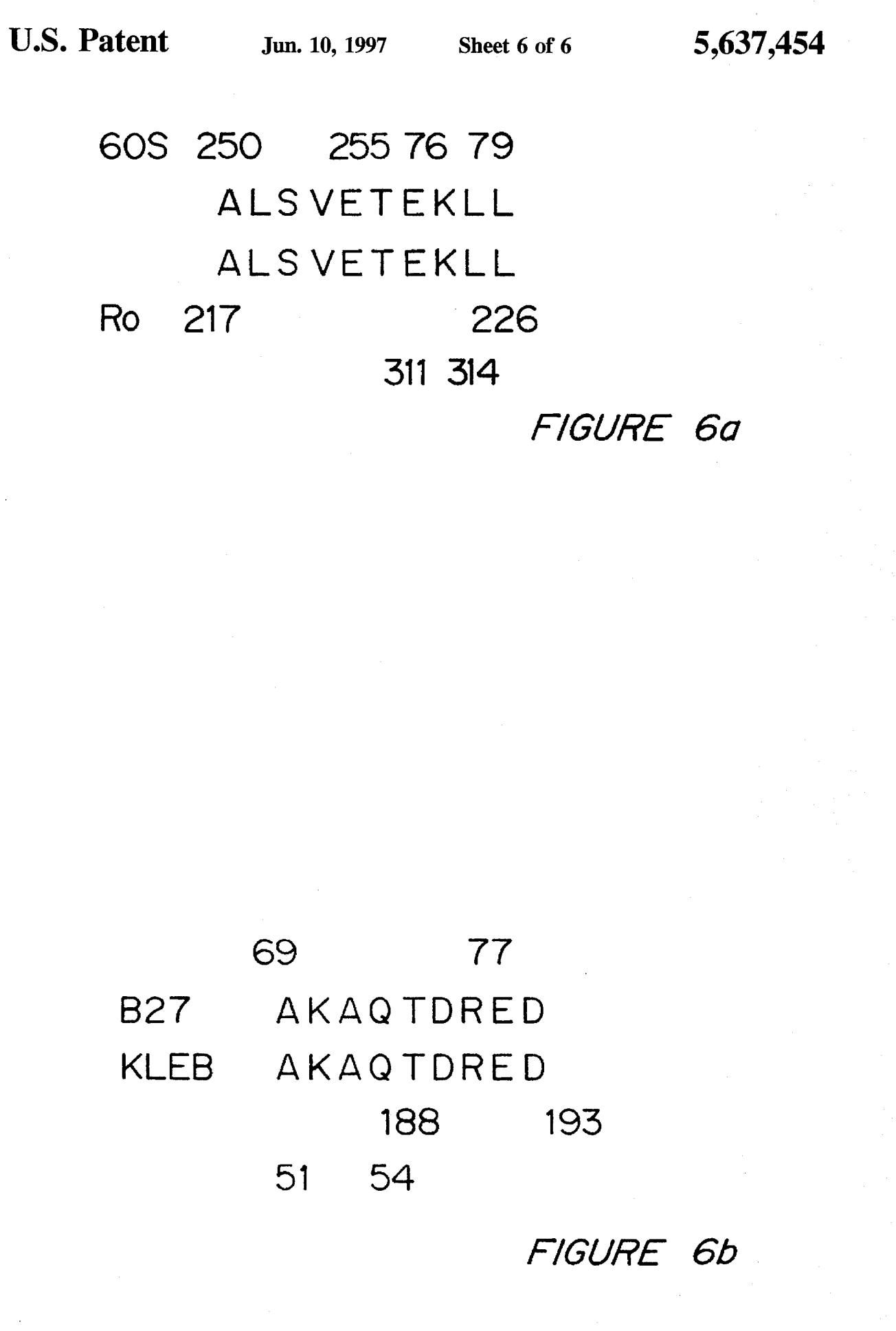

Another very interesting possible example of this phenomenon has been discovered in the Ro/SSA system. The human 60 S ribosomal phosphoprotein PO (access cede NW: A27125) is an autoantigen whose autoantibodies are related to psychiatric symptoms in SLE. This protein has specific homology with 60 kD Ro/SSA. In reviewing the homologous regions there is a 10 amino acid stretch of Ro/SSA which is composed of two regions of PO (FIG. 6A). Perhaps there is an immunologic interaction between the two proteins based upon the juxtaposition of homologous region.

Moreover, the E K L L sequence is found in this and a second region of Ro/SSA.

The interaction between Klebsiella neuramidase and HLA-B27 in ankylosing spondylitis is another potential example. Previously, a six amino acid stretch of homology has been appreciated. A second region of homology originating at a disparate site in the Klebsiella protein which abuts the previously appreciated homologous hexapeptide region in B27 has been found (FIG. 6B). Perhaps the juxtaposition of the two neuramidase sequences in the HLA-B27 sequence influences the relationship of spondolytis to HLA-B27 and the appearance and expression of this disease.

In scleroderma, autoantibodies binding topoisomerase (scl-70) and the centromere are common but both specificities tend not to be found in the same patient. One approach according to the present invention would be to perform a homology search and to evaluate the antigenicity of short peptides (probably octapeptides) from both of these autoantigens. Then an analysis similar in procedure to the one performed with Ro/SSA would be pursued. The proteins satisfying the short peptide homology rules would be sought. Then the probability of homology of the query sequences coinciding with antigenicity in the autoantigen will be assessed. This will then be used to construct hypotheses of antecedent antigen(s), or immunogens, or possible infection.

EXAMPLE 8

Animal Model for screening compounds for treatment of autoimmune diseases

An animal model was developed which represents not only the successful induction of the production of human autoantibodies in an animal, but may provide a means for screening of compounds which inhibit the production by these cells of the autoantibodies or neutralization in vivo of the effects of the autoantibodies. It also serves as a tool in the study of the production of these antibodies, allowing experiments which cannot be performed in humans due to the unacceptable risk involved. For example, these animals can be injected with antigen to the autoantibodies to determine if the antigen elicits a still greater response or if the antigen can be used to neutralize circulating antibody. These animals can be infected with viruses. They can also be used to determine the requirements which perpetuate the immune disorder.

Severe Combined Immunodeficient Mice. Adult retired breeder mice C.B-17 SCID (homozygous for SCID mutation) were bred and maintained in a sterile environment at the Oklahoma Medical Research Foundation. All SCID mice were 24 weeks of age or older at the time of injection. Mice were removed from the sterile environment and injected with human peripheral blood mononuclear cells. Mice were subsequently fed standard non-sterile mouse chow and kept in isolation laminar flow cubicles (BioClean, Inc.). SCID mice were bled by tail vein.

Isolation of human peripheral blood mononuclear cells. After obtaining informed consent, venipuncture was performed on patients with SLE, primary bilary cirrhosis (PBC), and a normal volunteer. Approximately 150 ml of blood was withdrawn into a heparinized container (preservative-free). Mononuclear cells were separated by low speed density centrifugation (Histopak, Sigma Chemical Co., St. Louis, Mo.). Viability was determined by exclusion of trypan blue. Various numbers ($2\times10^6$ to $50\times^6$) of isolated human mononuclear cells were injected intraperitoneally.

Enzyme linked immunosorbent assays ELISA). These assays were performed using established techniques, as described by Gaither and Harley, *Protides Biol. Fluids Proc. Colloq.* 33, 413 (1985), to screen for the production of human IgG and specific autoantibodies. To screen for human IgG production, 96 well microtiter plates were coated with mouse serum at limiting dilutions. They were subsequently washed, blocked and goat anti-human IgG (gamma chain specific) alkaline phosphatase conjugate (Sigma Chemical Co., St. Louis, Mo.) was added. After overnight incubation, microtiter plates were washed, substrate added and optical density readings taken on an ELISA reader (Beckman Instruments).

Engrafted mouse sera were screened for autoantibodies using a standard anti-Ro/SSA ELISA which relied upon highly purified Ro/SSA as described by Mamula, et al., *J. Exp. Med.* 86:1889 (1986).

Indirect immunofluorescent anti-nuclear antibodies. SLE, primary biliary cirrhosis, normal human sera, and engrafted mouse sera were analyzed for anti-nuclear antibodies on Hep-2 cells using a NOVA Lite ANA (INOVA DIAGNOSTICS, Inc., San Diego, Calif.). Serum samples were diluted and 50–75 μl were applied to each substrate slide. After 30 rain incubation in a moist chamber at room temperature, the slides were thoroughly washed with PBS. Goat anti-human IgG gamma chain specific FITC conjugate (Sigma Chemical Co., St. Louis, Mo.) is added at 1:7500 dilution and incubated for 30 rain at room temperature. Slides were subsequently washed with PBS and immunofluorescent staining visualized under a fluorescence microscope.

C.B -17 SCID mice were injected intraperitoneally with sterile human peripheral blood mononuclear cells at various concentrations. Peripheral blood mononuclear cells were isolated from a reference patient who had the clinical diagnosis of systemic lupus erythematosus (SLE) and had precipitating antibodies to Ro(SSA) and La(SSB). Previous clinical studies of this patient had shown a positive ANA with a speckled nuclear pattern at titers of 1:3240. A normal sex and age matched control was identified and an identical number of peripheral blood mononuclear cells were injected intraperitoneally into SCID mice. This control individual displayed no clinical signs or symptoms of rheumatic disease, had no precipitating autoantibodies to Ro(SSA) nor La(SSB) and had a negative ANA by immunofluorescence. Peripheral blood mononuclear cells were also isolated and subsequently injected into SCID mice from a patient who had primary biliary cirrhosis with a positive immunofluorescent anti-mitochondrial staining pattern at a titer of 1:12,960.

To monitor the engraftment of human cells and their subsequent antibody production, engrafted mice (those mice which received intraperitoneal human mononuclear cells) were bled 14 weeks after injection and their sera screened using ELISA for production of human IgG. Two of the four mice injected with normal human mononuclear cells were positive in the ELISA screen for IgG, the ones injected with $50\times10^6$ cells. The two mice injected with $5\times10^6$ and $1\times10^6$ mononuclear cells showed no human IgG. Similarly, two of the four SLE mice ($50\times10^6$) showed human IgG production and the other two showed no ELISA activity. Human sera from the SLE patient demonstrated approximately 100-fold more activity than that seen in engrafted mice while preimmune or sham (saline injected) mice were devoid of activity. Subsequent bleedings of engrafted mice at 21 weeks demonstrated stable levels of human IgG.

Indirect immunofluorescent studies were done on engrafted mouse sera to screen for the presence of anti-nuclear and anti-cytoplasmic antibodies. Of the two SLE engrafted mice which were positive in the human IgG screening assay, the one injected with $50\times10^6$ cells gave a positive speckled nuclear staining pattern while sham mice showed no immunofluorescence. However, the SLE mouse injected with $25\times10^6$ cells failed to have a positive immunofluorescence.

A single SCID mouse serum reconstituted with $50\times10^6$ cells from a patient with primary biliary cirrhosis was also tested for anti-nuclear antibodies. This serum demonstrated a diffuse cytoplasmic staining pattern without staining nuclear material which appeared identical to that of the patient.

In order to further define the antibody response in these reconstituted SCID mice, ELISA were performed testing for the presence of anti-Ro/SSA and anti-L,a/SSB. Again, the SLE engrafted mouse ($50\times10^6$) demonstrated positive immunoreactivity in ELISA at serum dilutions of $10^{-2}$. None of the other SLE engrafted mice or normal volunteer engrafted mice, pre-immune mouse sera, or sham treated mice showed reactivity.

To validate the specificity of this immunoreactivity, SLE engrafted mouse sera were incubated with purified bovine Ro(SSA) and human Ro(SSA). Subsequently, samples were analyzed in ELISA and the response was shown to be completely inhibitable, thereby validating the specificity of antibody binding to the Ro(SSA) antigen.

Modification and variations of the methods and composition of the present invention will be obvious to those skilled in the art from the foregoing detailed description of the invention. Such modifications and variations are intended to come within the scope of the following claims.

I claim:

1. A method for determining a potential immunogenic agent in a disease characterized by the production of autoantibodies or autoantigen-specific T cell receptors comprising:

identifying a self-antigen bound by a population of autoantibodies or autoantigen-specific T cell receptors present in a patient having the disease;

identifying amino acid sequences of the self-antigen immunoreactive with the autoantibodies or autoantigen-specific T cell receptors;

comparing the self-antigen amino acid sequences with amino acid sequences of potential immunogenic agents to identify potential immunogenic agents as proteins containing two or more regions of sequence homologous with the self-antigen;

determining the potential immunogenic agents having two or more regions of sequence homology which are immunoreactive with the autoantibodies or autoantigen-specific T cell receptors; and determining that the extent of correlation of the two or more regions of sequence in a first potential immunogenic agent with the regions of sequence of the self-antigen is statistically significant as compared with the extent of correlation between the regions of sequence of the self-antigen and two or more regions of sequence of a second potential immunogenic agent having sequence homology and that it is therefore likely that the first potential immunogenic agent induces the production of the autoantibodies or autoantigen specific T-cell receptors.

2. The method of claim 1 wherein overlapping peptides of the self-antigen of no more than twenty amino acids are synthesized for correlating regions of homology between the self-antigen and potential immunogenic agents with antigenicity, wherein antigenicity is determined by reacting the overlapping peptides with the autoantibody or autoantigen-specific T cell receptor.

3. The method of claim 1 wherein the autoantibody or autoantigen-specific T cell receptor is anti-Ro/SSA, the self-antigen is Ro/SSA, and the potential immunogenic agents are vesicular stomatitis virus proteins.

4. The method of claim 1 further comprising isolating self-antigen, wherein the self-antigen is immunoreactive with autoantibodies or autoantigen-specific T cell receptors from patients having autoimmune disease, by immunoreaction with molecules specifically immunoreactive with a self-antigen selected from the group consisting of immunoglobulins, antigen specific B cell surface receptors, and antigen specific T cell receptors.

5. The method of claim 1 further comprising synthesizing amino acid sequences of the potential immunogenic agent consisting of no more than twenty amino acids for determination of antigenicity of regions of the potential immunogenic agent.

6. The method of claim 1 further comprising classifying regions of the self-antigen on the basis of antigenicity as determined by immunoreactivity with autoantibodies or autoantigen-specific T cell receptors and homology to the potential immunogenic agent, having antigenicity as determined by immunoreactivity with autoantibodies or autoantigen-specific T cell receptors but not homology to the potential immunogenic agent, having homology to the potential immunogenic agent but not antigenicity, and having neither homology with the potential immunogenic agent nor reactivity with the autoantibodies or autoantigen-specific receptors.

7. The method of claim 1 further comprising classifying regions of the potential immunogenic agent on the basis of having antigenicity as determined by immunoreactivity with antibodies or autoantigen-specific T cell receptors and homology to the antigen, having antigenicity as determined by reaction with antibodies or autoantigen-specific T cell receptors but not homology to the self-antigen, having homology to the self-antigen but not antigenicity, and having neither homology to the self-antigen nor immunoreactivity with the antibodies or autoantigen-specific T cell receptors.

8. The method of claim 1 wherein regions of homology with the self-antigen and antigenicity based on immunoreaction with autoantibodies or autoantigen-specific T sell receptors are found in a protein expressed or caused to be expressed by an infectious agent selected from the group consisting of viruses, viroids, bacteria, Rickettsia, and fungi, further comprising immunoreacting other proteins from the infectious agent with additional autoantibodies or autoantigen-specific specific T cell receptors from the patient or other patients having the same disease.

9. The method of claim 1 wherein the disease is selected from the group of disorders characterized by production of autoantibodies and disorders characterized by manifestation of symptoms associated with the presence of circulating autoantibody.

10. A method for assaying for patients having an infection resulting in manifestation of immune disorders comprising (a) reacting (i) a vesicular stomatitis viral protein or peptide component thereof including two or more antigenic regions immunoreactive with a molecule selected from the group consisting of antibodies, R cell surface receptors, and antigen specific T cell receptors, which is immunoreactive with a self-antigen, wherein the antigenic regions are homologous to two or more regions of a protein expressed by or caused to be expressed by vesicular stomatitis virus, (ii) reagents for detecting an immunoreaction between the peptide component and molecules selected from the group consisting of antibodies, B cell surface receptors or antigen specific T cell receptors in a biological sample from the patient, and (iii) a sample of biological fluid or tissue from the patient, and (b) determining if there is a molecule in the patient sample that is immunoreactive with the vesicular stomatitis viral protein or peptide component thereof.

11. The method of claim 10 wherein the patient is being screened for a rhabdovirus infection comprising immunoreacting a protein or peptide component thereof immunoreactive with antibodies to vesicular stomatitis virus, with a sample of a biological fluid or tissue from the patient.

* * * * *

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:1:

```
Glu Tyr Arg Lys Lys Met Asp Ile
1               5
```

( 2 ) INFORMATION FOR SEQ ID NO:2:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:2:

```
Ala Ile Ala Leu Arg Glu Tyr Arg Lys Lys Met Asp Ile Pro Ala
1               5                   10                  15
```

( 2 ) INFORMATION FOR SEQ ID NO:3:

-continued ( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:3:

Thr Asn Thr Pro Ala Asp Val Phe Ile Val Phe Thr Asp
1 5 10

( 2 ) INFORMATION FOR SEQ ID NO:4:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:4:

Val His Pro Ala Ile Ala Leu Arg Glu Tyr Arg Lys Lys Met Asp Ile
1 5 10 15

( 2 ) INFORMATION FOR SEQ ID NO:5:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:5:

Ala Leu Asp Val Ile Arg Asn Phe Thr Leu
1 5 10

( 2 ) INFORMATION FOR SEQ ID NO:6:

( i ) SEQUENCE CHARACTERISTICS:
( A ) LENGTH: 8 amino acids
( B ) TYPE: amino acid
( C ) STRANDEDNESS: single -continued ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:6:

Glu Tyr Arg Lys Lys Met Asp Ile
1 5

( 2 ) INFORMATION FOR SEQ ID NO:7:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:7:

Cys Ala Leu Arg Glu Tyr Arg Lys Lys Met Asp Ile Pro Ala
1 5 10

( 2 ) INFORMATION FOR SEQ ID NO:8:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:8:

Glu Lys Gln Ile Ala Asn Ser Gln Asp Gly Tyr Val Trp Gln Val Thr
1 5 10 15

Asp ( 2 ) INFORMATION FOR SEQ ID NO:9:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:9:

Tyr Lys Gly Glu Trp Lys Pro Gln Ile Asp Asn Pro Asp Tyr Lys Gly
1 5 10 15

Thr ( 2 ) INFORMATION FOR SEQ ID NO:10:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:10:

Glu Asp Lys Glu Glu Asp Glu Glu Glu Asp Val Pro Gly Gln Ala Lys
1 5 10 15

Asp Glu Leu ( 2 ) INFORMATION FOR SEQ ID NO:11:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:11:

Glu Tyr Arg Lys Lys Leu Met Asp
1 5

( 2 ) INFORMATION FOR SEQ ID NO:12:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide -continued ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:12:

Glu Tyr Arg Lys Lys Met Asp
1 5

( 2 ) INFORMATION FOR SEQ ID NO:13:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:13:

Val His Val Asn Asn
1 5

( 2 ) INFORMATION FOR SEQ ID NO:14:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:14:

Leu Lys Lys Ile
1

( 2 ) INFORMATION FOR SEQ ID NO:15:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:15:

Lys Gly Lys Gly Lys Gly
1 5

( 2 ) INFORMATION FOR SEQ ID NO:16:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:16:

Gly Lys Gly Lys
1

( 2 ) INFORMATION FOR SEQ ID NO:17:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:17:

Lys Ser Lys Glu
1

( 2 ) INFORMATION FOR SEQ ID NO:18:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:18:

-continued

Leu Thr Ala Leu Leu Leu Arg
1 5

( 2 ) INFORMATION FOR SEQ ID NO:19:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:19:

Arg Gly Lys Leu Asp Lys Asp Trp
1 5

( 2 ) INFORMATION FOR SEQ ID NO:20:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:20:

Leu Lys Ala Leu Asp
1 5

( 2 ) INFORMATION FOR SEQ ID NO:21:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:21:

Asp Glu Met Val
1

( 2 ) INFORMATION FOR SEQ ID NO:22:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:22:

Lys Leu Leu Asp Gly Leu Glu Asn
1 5

( 2 ) INFORMATION FOR SEQ ID NO:23:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:23:

Leu Thr Ala Leu Leu
1 5

( 2 ) INFORMATION FOR SEQ ID NO:24:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:24:

Thr Thr Glu Lys Asp Leu Ser
1 5

( 2 ) INFORMATION FOR SEQ ID NO:25:

( i ) SEQUENCE CHARACTERISTICS:
( A ) LENGTH: 4 amino acids
( B ) TYPE: amino acid (C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
(A) ORGANISM: Homo sapiens (xi) SEQUENCE DESCRIPTION: SEQ ID NO:25:

Tyr Arg Lys Lys
1

(2) INFORMATION FOR SEQ ID NO:26:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
(A) ORGANISM: Homo sapiens (xi) SEQUENCE DESCRIPTION: SEQ ID NO:26:

Lys Asp Leu Lys
1

(2) INFORMATION FOR SEQ ID NO:27:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
(A) ORGANISM: Homo sapiens (xi) SEQUENCE DESCRIPTION: SEQ ID NO:27:

Asp Pro Asp Asp
1

(2) INFORMATION FOR SEQ ID NO:28:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:28:

Ala Ala Ala Met
1

( 2 ) INFORMATION FOR SEQ ID NO:29:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:29:

Leu Ser His Leu Gln Lys
1 5

( 2 ) INFORMATION FOR SEQ ID NO:30:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:30:

Arg Thr Lys Asp Ala Glu
1 5

( 2 ) INFORMATION FOR SEQ ID NO:31:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal -continued ( v i ) ORIGINAL SOURCE:
( A ) ORGANISM: Homo sapiens ( x i ) SEQUENCE DESCRIPTION: SEQ ID NO:31:

Glu Lys Asp Ser
1

( 2 ) INFORMATION FOR SEQ ID NO:32:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:32:

Glu Val Cys Arg
1

( 2 ) INFORMATION FOR SEQ ID NO:33:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:33:

Ala Ile Ala Leu Arg Glu Tyr Arg Lys Lys Met Asp Ile Pro Ala
1 5 10 15

( 2 ) INFORMATION FOR SEQ ID NO:34:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:34:

-continued

Val His Pro Ala Ile Ala Leu Arg
1 5

( 2 ) INFORMATION FOR SEQ ID NO:35:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:35:

Lys Leu Gly Leu Glu Asn
1 5

( 2 ) INFORMATION FOR SEQ ID NO:36:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:36:

Lys Asp Leu Lys
1

( 2 ) INFORMATION FOR SEQ ID NO:37:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:37:

Leu Thr Ala Leu Leu Arg
1 5

( 2 ) INFORMATION FOR SEQ ID NO:38:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:38:

Arg Gly Lys Leu Lys Trp
1 5

( 2 ) INFORMATION FOR SEQ ID NO:39:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:39:

Thr Arg Thr Glu Lys Asp Ser
1 5

( 2 ) INFORMATION FOR SEQ ID NO:40:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:40:

Leu Ser His Leu Lys
1 5

( 2 ) INFORMATION FOR SEQ ID NO:41:

( i ) SEQUENCE CHARACTERISTICS:
( A ) LENGTH: 5 amino acids
( B ) TYPE: amino acid -continued ( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
( A ) ORGANISM: Homo sapiens ( x i ) SEQUENCE DESCRIPTION: SEQ ID NO:41:

Arg Thr Lys Asp Glu
1 5